US010006880B2

(12) United States Patent
Heller

(10) Patent No.: US 10,006,880 B2
(45) Date of Patent: *Jun. 26, 2018

(54) TEST STRIPS HAVING CERIA NANOPARTICLE ELECTRODES

(71) Applicant: Abbott Diabetes Care Inc., Alameda, CA (US)

(72) Inventor: Adam Heller, Austin, TX (US)

(73) Assignee: Abbott Diabetes Care Inc., Alameda, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/429,268

(22) PCT Filed: Sep. 20, 2013

(86) PCT No.: PCT/US2013/060995
§ 371 (c)(1),
(2) Date: Mar. 18, 2015

(87) PCT Pub. No.: WO2014/047484
PCT Pub. Date: Mar. 27, 2014

(65) Prior Publication Data
US 2015/0247817 A1 Sep. 3, 2015

Related U.S. Application Data

(60) Provisional application No. 61/704,404, filed on Sep. 21, 2012, provisional application No. 61/704,374, filed on Sep. 21, 2012, provisional application No. 61/711,686, filed on Oct. 9, 2012, provisional application No. 61/730,859, filed on Nov. 28, 2012.

(51) Int. Cl.
*G01N 27/327* (2006.01)
*G01N 27/30* (2006.01)
*B82Y 30/00* (2011.01)
*A61B 5/145* (2006.01)
*A61B 5/1486* (2006.01)

(52) U.S. Cl.
CPC ......... *G01N 27/3278* (2013.01); *A61B 5/145* (2013.01); *A61B 5/14532* (2013.01); *B82Y 30/00* (2013.01); *G01N 27/301* (2013.01); *G01N 27/3272* (2013.01); *A61B 5/1486* (2013.01); *A61B 5/14503* (2013.01); *A61B 5/14539* (2013.01); *A61B 5/14542* (2013.01); *A61B 5/14865* (2013.01); *A61B 2562/0209* (2013.01)

(58) Field of Classification Search
CPC . A61B 5/14532; A61B 5/145; A61B 5/14503; A61B 5/14539; A61B 5/14542; A61B 5/14865; A61B 5/1486; B82Y 30/00; G01N 27/301; G01N 27/3278; G01N 27/3272
See application file for complete search history.

(56) References Cited

U.S. PATENT DOCUMENTS

| | | | |
|---|---|---|---|
| 4,545,382 A | 10/1985 | Higgins et al. | |
| 4,711,245 A | 12/1987 | Higgins et al. | |
| 5,262,035 A | 11/1993 | Gregg et al. | |
| 5,262,305 A | 11/1993 | Heller et al. | |
| 5,264,104 A | 11/1993 | Gregg et al. | |
| 5,320,725 A | 6/1994 | Gregg et al. | |
| 5,356,786 A | 10/1994 | Heller et al. | |
| 5,509,410 A | 4/1996 | Hill et al. | |
| 5,593,852 A | 1/1997 | Heller et al. | |
| 5,601,435 A | 2/1997 | Quy | |
| 5,628,890 A | 5/1997 | Carter et al. | |
| 5,820,551 A | 10/1998 | Hill et al. | |
| 5,822,715 A | 10/1998 | Worthington et al. | |
| 5,899,855 A | 5/1999 | Brown | |
| 5,918,603 A | 7/1999 | Brown | |
| 6,071,391 A | 6/2000 | Gotoh et al. | |
| 6,121,009 A | 9/2000 | Heller et al. | |
| 6,134,461 A | 10/2000 | Say et al. | |
| 6,143,164 A | 11/2000 | Heller et al. | |
| 6,144,837 A | 11/2000 | Quy | |
| 6,161,095 A | 12/2000 | Brown | |
| 6,175,752 B1 | 1/2001 | Say et al. | |
| 6,270,455 B1 | 8/2001 | Brown | |
| 6,284,478 B1 | 9/2001 | Heller et al. | |
| 6,377,894 B1 | 4/2002 | Deweese et al. | |
| 6,413,489 B1 * | 7/2002 | Ying | B01J 13/0056 423/600 |

(Continued)

FOREIGN PATENT DOCUMENTS

WO 2012/041507 4/2012

OTHER PUBLICATIONS

Ohara et al. (1993) "Glucose electrodes based on cross-linked bis(2,2'-bipyridine)chloroosmium(=/2=) complexed poly(1-vinylimidazole) films" Anal. Chem. 65(23):3512-3517.

(Continued)

*Primary Examiner* — Gurpreet Kaur
(74) *Attorney, Agent, or Firm* — Meunier Carlin & Curfman LLC

(57) ABSTRACT

Ceria nanoparticle compositions for use with in vitro electrochemical chemical or biochemical sensors (e.g., test strip glucose sensors), for example to form a cathode or a reference electrode, are provided. The ceria nanoparticle compositions may be combined with a conductive material (e.g., mixed with) to form the cathode or the reference electrode or the ceria nanoparticle compositions may be deposited over a layer of conductive material to form the cathode or the reference electrode. Electrochemical in vitro sensors for determining the concentration of an analyte having a reference electrode and/or a cathode including a ceria nanoparticle composition, and methods for determining an analyte concentration using the electrochemical sensors are also described. Methods of making in vitro electrochemical sensors having a reference electrode and/or a cathode including a ceria nanoparticle composition are also provided.

31 Claims, 14 Drawing Sheets

(56) References Cited

U.S. PATENT DOCUMENTS

| | | |
|---|---|---|
| 6,503,381 B1 | 1/2003 | Gotoh et al. |
| 6,514,460 B1 | 2/2003 | Fendrock |
| 6,514,718 B2 | 2/2003 | Heller et al. |
| 6,540,891 B1 | 4/2003 | Stewart et al. |
| 6,560,471 B1 | 5/2003 | Heller et al. |
| 6,579,690 B1 | 6/2003 | Bonnecaze et al. |
| 6,592,745 B1 | 7/2003 | Feldman et al. |
| 6,600,997 B2 | 7/2003 | Deweese et al. |
| 6,605,200 B1 | 8/2003 | Mao et al. |
| 6,605,201 B1 | 8/2003 | Mao et al. |
| 6,616,819 B1 | 9/2003 | Liamos et al. |
| 6,654,625 B1 | 11/2003 | Say et al. |
| 6,676,816 B2 | 1/2004 | Mao et al. |
| 6,730,200 B1 | 5/2004 | Stewart et al. |
| 6,736,957 B1 | 5/2004 | Forrow et al. |
| 6,746,582 B2 | 6/2004 | Heller et al. |
| 6,764,581 B1 | 7/2004 | Forrow et al. |
| 6,881,551 B2 | 4/2005 | Heller et al. |
| 6,893,545 B2 | 5/2005 | Gotoh et al. |
| 6,932,894 B2 | 8/2005 | Mao et al. |
| 7,090,756 B2 | 8/2006 | Mao et al. |
| 7,167,818 B2 | 1/2007 | Brown |
| 7,299,082 B2 | 11/2007 | Feldman et al. |
| 7,501,053 B2 | 3/2009 | Karinka et al. |
| 7,811,231 B2 | 10/2010 | Jin et al. |
| 7,822,557 B2 | 10/2010 | Chen et al. |
| 8,106,780 B2 | 1/2012 | Goodnow et al. |
| 8,172,997 B2 | 5/2012 | Seal et al. |
| 2002/0098119 A1* | 7/2002 | Goodman .......... G01N 33/0031 422/82.01 |
| 2005/0051440 A1* | 3/2005 | Simpson ............ A61B 5/14532 205/778 |
| 2006/0025662 A1 | 2/2006 | Buse et al. |
| 2006/0091006 A1 | 5/2006 | Wang et al. |
| 2006/0253012 A1* | 11/2006 | Petisce ................ B05D 1/02 600/347 |
| 2007/0042377 A1 | 2/2007 | Gao et al. |
| 2007/0068807 A1 | 3/2007 | Feldman et al. |
| 2007/0095661 A1 | 5/2007 | Wang et al. |
| 2007/0108048 A1 | 5/2007 | Wang et al. |
| 2007/0199818 A1 | 8/2007 | Petyt et al. |
| 2008/0066305 A1 | 3/2008 | Wang et al. |
| 2008/0102441 A1 | 5/2008 | Chen et al. |
| 2008/0148873 A1 | 6/2008 | Wang |
| 2008/0177164 A1 | 7/2008 | Heller et al. |
| 2008/0179187 A1 | 7/2008 | Ouyang et al. |
| 2008/0267823 A1 | 10/2008 | Wang et al. |
| 2009/0071848 A1* | 3/2009 | Seal ....................... C12Q 1/004 205/782 |
| 2009/0095625 A1 | 4/2009 | Forrow |
| 2010/0198034 A1 | 8/2010 | Thomas et al. |
| 2010/0213057 A1 | 8/2010 | Feldman et al. |
| 2010/0324392 A1 | 12/2010 | Yee et al. |
| 2010/0326842 A1 | 12/2010 | Mazza et al. |
| 2011/0003084 A1 | 1/2011 | Berghaus et al. |
| 2011/0048275 A1 | 3/2011 | Fletcher |
| 2011/0120865 A1 | 5/2011 | Bommakanti et al. |
| 2011/0124993 A1 | 5/2011 | Bommakanti et al. |
| 2011/0124994 A1 | 5/2011 | Bommakanti et al. |
| 2011/0126188 A1 | 5/2011 | Bernstein et al. |
| 2011/0210726 A1* | 9/2011 | Cui ....................... C12Q 1/004 324/252 |
| 2011/0213225 A1 | 9/2011 | Bernstein et al. |
| 2011/0256024 A1 | 10/2011 | Cole et al. |
| 2011/0257495 A1 | 10/2011 | Hoss et al. |
| 2012/0157801 A1 | 6/2012 | Hoss et al. |
| 2012/0245447 A1 | 9/2012 | Karan et al. |
| 2012/0257801 A1 | 10/2012 | Wada |
| 2012/0315659 A1* | 12/2012 | Andreescu ................ C12Q 1/26 435/25 |
| 2012/0323098 A1 | 12/2012 | Moein et al. |
| 2013/0045416 A1* | 2/2013 | Seferos ................ G01N 21/554 429/209 |
| 2014/0042038 A1* | 2/2014 | Bhansali ................ G01N 27/48 205/777.5 |

OTHER PUBLICATIONS

Feldman et al. (2003) "A continuous glucose sensor based on Wired Enzyme™ technology-Results from a 3-day trial in patients with type 1 diabetes." *Diabetes technology & therapeutics* 5.5:769-779.

Babu et al. (2009) "Dopant-mediated oxygen vacancy tuning in ceria nanoparticles" Nanotechnology 20:1-5.

Kosacki et al. (2002) "Raman scattering and lattice defects in nanocrystalline $CeO_2$ thin films" Solid State Ionics 149(1):99-105.

\* cited by examiner

3/21
CeO$_2$ -
ThA(0.1)
-H2$_O$
(1:2)

C

D

TEST STRIPS HAVING CERIA NANOPARTICLE ELECTRODES

CROSS-REFERENCE TO RELATED APPLICATIONS

This application claims priority based on U.S. Provisional Application No. 61/704,404, filed Sep. 21, 2012, U.S. Provisional Application No. 61/704,374, filed Sep. 21, 2012, U.S. Provisional Application No. 61/711,686, filed Oct. 9, 2012, and U.S. Provisional Application No. 61/730,859, filed Nov. 28, 2012, the disclosures of which are incorporated by reference herein in their entirety.

INTRODUCTION

In the management and diagnosis of diabetes, it is desirable or necessary to regularly monitor the concentration of particular constituents in a fluid. A number of systems are available that analyze the constituents of bodily fluids such as blood, urine and saliva. Examples of such systems conveniently monitor the level of particular medically significant fluid constituents, such as, for example, cholesterol, ketones, vitamins, proteins, and various metabolites or blood sugars, such as glucose. Diagnosis and management of patients suffering from diabetes mellitus, a disorder of the pancreas where insufficient production of insulin prevents normal regulation of blood sugar levels, requires carefully monitoring of blood glucose levels on a daily basis. A number of systems that allow individuals to easily monitor their blood glucose are currently available. Such systems include electrochemical biosensors, including those that have a glucose sensor that determine the concentration of an analyte, meaning a chemical or a biochemical, in a bodily aqueous fluid (e.g., blood, interstitial fluid, dermal fluid) sample. For example, many patients suffering of Type 1 diabetes monitor their blood glycemia (glucose concentration) five or more times a day, often using test strips, which are typically used only once.

Accordingly, it would be desirable to have systems that monitor the concentration of particular constituents in a fluid, such as glucose

SUMMARY

Ceria nanoparticle compositions for use with in vitro electrochemical chemical or biochemical sensors (e.g., test strip glucose sensors), for example to form a cathode or a reference electrode, are provided. The ceria nanoparticle compositions may be combined with a conductive material (e.g., mixed with) to form the cathode or the reference electrode or the ceria nanoparticle compositions may be deposited over a layer of conductive material to form the cathode or the reference electrode. Electrochemical in vitro test strips for monitoring the concentration of an analyte having a reference electrode and/or a cathode including a ceria nanoparticle composition, and methods for monitoring an analyte concentration using the electrochemical test strips are also described. Methods of making in vitro electrochemical test strips having a reference electrode and/or a cathode including a ceria nanoparticle composition are also provided.

DETAILED DESCRIPTION

Figure 1:
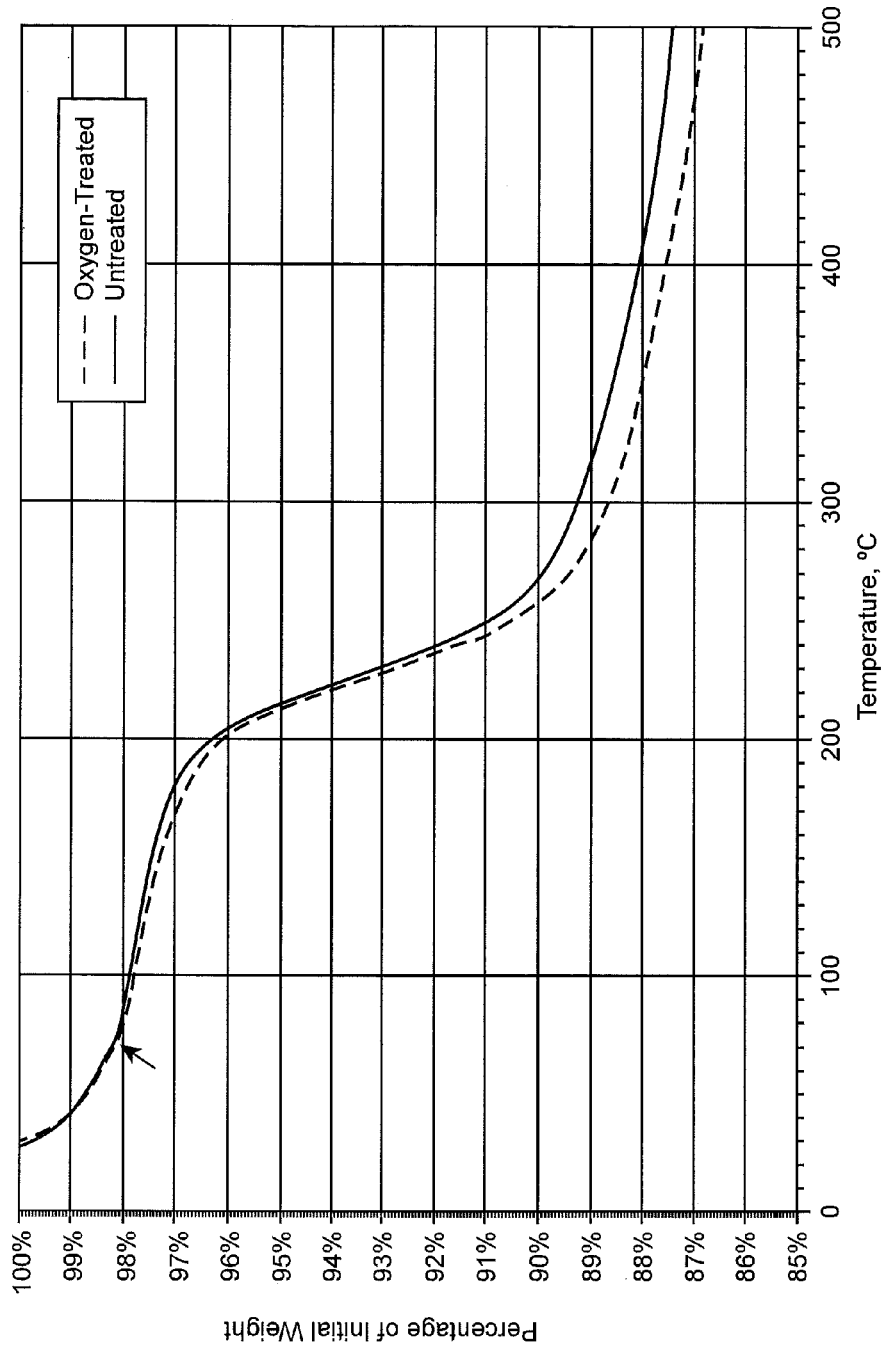
FIG. 1 shows an example thermogravimetric mass loss curves for ceria nanoparticles obtained from their non-oxygenated and oxygenated solutions.

Ceria nanoparticle compositions for use with in vitro electrochemical chemical or biochemical sensors (e.g., test strip glucose sensors), for example to form a cathode or a reference electrode, are provided. In this application ceria means any oxide of cerium. The oxide can have the composition $CeO_{2-x}$. The value of x can range from 0 to 0.5. When x=0, the composition is $CeO_2$ and the cation is $Ce^{4+}$. When x=0.5, the composition is $Ce_2O_3$ and the cation is $Ce^{3+}$. The $Ce^{4+}$ and $Ce^{3+}$ cations can be in the bulk of the nanoparticles or at their surface, meaning at their interface with the analyzed solution, which is usually an aqueous solution. Usually the cations at or near the solution interface are more redox active, wherefore the redox activity increases as the particle size is decreased. Typically, the fraction of redox active cations increases with the inverse of the size of the nanoparticle. Therefore, compositions with particle sizes smaller than 5 nm are preferred over compositions with particle sizes smaller than 10 nm, and compositions with particle sizes smaller than 10 nm are preferred over compositions with particle sizes smaller than 20 nm, etc.

Before the conductive electroreducible nanoparticle oxidant compositions, electrochemical test strips and methods of the present disclosure are described in greater detail, it is to be understood that the test strips and methods are not limited to particular embodiments described, as such may, of course, vary. It is also to be understood that the terminology used herein is for the purpose of describing particular embodiments only, and is not intended to be limiting, since the scope of the test strips and methods will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the test strips and methods. The upper and lower limits of these smaller ranges may independently be included in the smaller ranges and are also encompassed within the test strips and methods, subject to any specifically excluded limit in the stated range. Where the stated range includes one or both of the limits, ranges excluding either or both of those included limits are also included in the test strips and methods.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which the methods belong. Although any methods and materials similar or equivalent to those described herein can also be used in the practice or testing of the test strips and methods, representative illustrative test strips, methods and materials are now described.

All publications and patents cited in this specification are herein incorporated by reference as if each individual publication or patent were specifically and individually indicated to be incorporated by reference and are incorporated herein by reference to disclose and describe the test strips, methods and/or materials in connection with which the publications are cited. The citation of any publication is for its disclosure prior to the filing date and should not be construed as an admission that the present test strips and methods are not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Certain features of the electrodes, test strips and methods, which are, for clarity, described in the context of separate embodiments, may also be provided in combination in a single embodiment. Conversely, various features of the test strips and methods, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed, to the extent that such combinations embrace operable processes and/or devices/systems/kits. In addition, all sub-combinations listed in the embodiments describing such variables are also specifically embraced by the present test strips and methods and are disclosed herein just as if each and every such sub-combination was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present test strips and methods. Any recited method can be carried out in the order of events recited or in any other order which is logically possible.

Ceria Nanoparticle Compositions

As summarized above, compositions having ceria nanoparticles and electrochemical test strips that use ceria nanoparticle compositions are disclosed. The ceria nanoparticle compositions may be employed in an electrochemical analyte test strip such as on a surface of a conductive or non-conductive substrate to form a cathode or reference electrode of the electrochemical analyte test strips.

In embodiments of the present disclosure, ceria nanoparticle compositions include ceria nanoparticles. The term "ceria" is used in its conventional sense to refer any oxide of cerium, such as solid cerium oxide and can have oxidation states of +3 (cerium III) and +4 (cerium IV) in any ratio. Ceria nanoparticles are described by the formula $CeO_{2-x}$, where x ranges from 0 to 0.5 depending on the number of cerium atoms in the crystalline lattice having a valence of +3 and cerium atoms having a valence of +4. Accordingly, embodiments according to the certain aspects include compositions having ceria nanoparticles of the formula $CeO_{2-x}$ where x is 0.1 or greater, such as 0.15 or greater, such as 0.2 or greater, such as 0.25 or greater, such as 0.30 or greater, such as 0.35 or greater, such as 0.4 or greater, such as 0.45 or greater, such as 0.49 or greater and including ceria nanoparticles of the formula $CeO_{2-x}$ where x is 0.5. In certain embodiments, cerium atoms in ceria nanoparticles according to the present disclosure have a valence of +3 (i.e., ceria nanoparticles of the formula $Ce_2O_3$).

Compositions of interest may include one or more forms of ceria nanoparticles. For example, a given composition may include ceria nanoparticles of the formula $CeO_{2-x}$ where x varies from 0.01 to 0.5. In other instances, depending on the source of ceria, storage conditions, and the desired electrode (e.g., cathode or reference electrode) properties, compositions may include particular forms of ceria nanoparticles. In some instances ceria nanoparticles having a value of x between about 0.01 and 0.2 may be 50% or greater of the total weight of ceria nanoparticles in the composition, such as 60% or greater, such as 75% or greater, such as 90% or greater, such as 95% or greater and including 99% or greater of the total weight of ceria nanoparticles in the composition. In other embodiments, ceria nanoparticles having a value of x of 0.2 or greater may be 50% by weight or greater of the total weight of ceria nanoparticles in the composition, such as 60% by weight or greater, such as 75% by weight or greater, such as 90% by weight or greater, such as 95% by weight or greater and including 99% by weight or greater. In yet other instances, ceria nanoparticles having a value of x of 0.5 may be 50% by weight or greater of the total weight of ceria nanoparticles in the composition, such as 60% by weight or greater, such as 75% by weight or greater, such as 90% by weight or greater, such as 95% by weight or greater and including 99% by weight or greater.

As such, depending on the type of electrode (e.g., reference electrode or cathode) employing the ceria nanoparticle compositions described herein, the valence state of the ceria nanoparticles bulk and/or of their surface may vary. In certain embodiments, ceria nanoparticles and/or ceria nanoparticle surfaces in the ceria nanoparticle composition are electroreducible. The term "electroreducible" is used herein in its conventional sense to refer to a state in which the $Ce^{4+}$ in the ceria nanoparticles or at their surface can act as an oxidant (i.e., accept one or more electrons). For example, in embodiments in which a ceria nanoparticle composition is used to form a cathode, the ceria nanoparticles may be at least mostly electroreducible. In other embodiments, ceria nanoparticles and/or their surfaces in the ceria nanoparticle composition are electroxidizable. The term "electrooxidizable" is used herein in its conventional sense to refer to a state in which the ceria nanoparticles can act as a reductant (i.e., donate one or more electrons). In yet other embodiments, ceria nanoparticles in the ceria nanoparticle composition may be both electroreducible and electrooxidizable (i.e., mixed valence, can accept or donate electrons). For example, in endowments in which a ceria nanoparticle composition is used to form a reference electrode, the ceria nanoparticles, and/or their surfaces, may be both electroreducible and electrooxidizable.

Ceria nanoparticles according to the present disclosure may include lattice defect sites, often at or near the surface of the nanoparticles, which allow oxygen absorption by the ceria nanoparticles. By "lattice defect" is meant irregularities in the three-dimensional structure which gives rise to vacancies within the crystalline lattice so that ceria nanoparticles are capable of storing oxygen. Lattice defects are typically at or near the surface of the nanocrystallites, and may also include, but are not limited to, oxygen anion vacancy defects, self-interstitials, interstitial impurity atoms and edge dislocations. Nanoparticle surfaces, meaning their solution interfaces, are considered here to be "lattice defects" as are boundaries between nanocrystallytes constituting the nanoparticles.

In some embodiments, compositions may include ceria nanoparticles having oxygen anion vacancy defects. By "oxygen anion vacancy defect" is meant a vacant site of the crystalline lattice where an $O^{2-}$ anion would occupy in a $CeO_2$ lattice. The amount of oxygen anion vacancy defects in ceria nanoparticles of certain compositions may vary depending on the desired oxygen loading and may be 1% or more of oxygen sites in the crystalline structure, such as 2% or more, such as 3% or more, such as 5% or more, such as 10% or more, such as 15% or more and including 20% or more of the oxygen sites in the crystalline structure may be vacant to facilitate the storage of oxygen.

In other embodiments, ceria nanoparticle compositions of interest include ceria nanoparticles having lattice defect sites, such as for example, by doping the ceria nanoparticle with one or more dopants. For example, compositions may include ceria nanoparticles doped with one or more of lanthanum, gadolinium, samarium, ytterbium, copper, manganese, zinc, cobalt, praseodymium, calcium, zirconium, aluminum, terbium, combinations thereof, among other dopants. Ceria nanoparticles may be doped with an amount of dopant to produce ceria nanoparticles having 1 mole percent or more dopant, such as 2 mole percent or more, such as 3 mole percent or more, such as 5 mole percent or more, such as 10 mole percent or more, such as 15 mole percent or more, such as 20 mole percent or more and including 25 mole percent or more of the dopant. Where ceria nanoparticles include two or more dopants, the amount of each dopant may vary depending on the oxygen loading desired. For example, each dopant may be 1 mole percent or more, such as 2 mole percent or more, such as 3 mole percent or more, such as 5 mole percent or more, such as 8 mole percent or more, such as 10 mole percent or more, and including 12 mole percent or more.

The amount of absorbed oxygen loaded into the nanoparticles may vary depending on the particle size, increasing when the particles are smaller and on the number of lattice vacancies as well other properties of the ceria nanoparticles. The amount of absorbed oxygen loaded into the subject ceria nanoparticles may be 0.1 percent by weight or more, such as 0.2 percent by weight or more, such as 0.3 percent by weight or more, such as 0.5 percent by weight or more and including an oxygen loading of 1 percent by weight or more. Where the ceria nanoparticle composition is employed in reference electrodes, the ceria nanoparticles may be heated to at temperature higher than about 200° C. or 300° C., for example to 400° C., in an oxygen-free atmosphere in order to cause the ceria nanoparticles to lose $O_2$ such that the resulting reference electrode provides a more precisely defined electrode potential. For example, coating of an electrode produced with mixture of ceria nanoparticles heated to 400° C., carbon black conductive material and a polymer can provide a 70 mV (Ag/AgCl) electrode, where Ag/AgCl is the potential of the Ag/AgCl electrode in 3 M KCl.

The average size of ceria nanoparticles in a given composition may vary and are therefore polydisperse, having diameters ranging from 1 nm to 100 nm, such as 2 nm to 50 nm, such as 2 nm to 25 nm, such as 3 nm to 20 nm, such as 5 nm to 20 nm, such as 10 nm to 20 nm or 5 nm to 10 nm. For example, ceria nanoparticles may have diameters ranging from 2 nm to 10 nm. Alternatively, ceria nanoparticles may have diameters ranging from 10 nm to 20 nm or from 20 nm to 50 nm. In general, the smaller diameter nanoparticles are preferred. For example, nanoparticles of diameters between 2 nm and 5 nm are preferred over nanoparticles of diameters between 5 nm and 10 nm which are preferred over nanoparticles with diameters between 10 nm and 20 nm which are preferred over nanoparticles with diameters between 20 nm and 50 nm.

In certain embodiments, compositions include ceria nanoparticles which have a narrow range of sizes such that the ceria nanoparticles in a given composition are all similar in size and deviation from the average particle size is no greater than 5 nm, such as no greater than 4 nm, such as no greater than 3 nm. For example, a given composition according to certain embodiments may include ceria nanoparticles which have sizes ranging from 1 nm to 5 nm, from 5 nm to 10 nm, from 10 nm to 15 nm, from 15 nm to 20 nm, including from 20 nm to 25 nm. In other embodiments, compositions may include ceria nanoparticles which have sizes ranging from 1 nm to 2.5 nm, from 2.5 nm to 5 nm, from 5 nm to 7.5 nm, from 7.5 nm to 10 nm, from 10 nm to 12.5 nm and including from 12.5 nm to 15 nm. In certain embodiments, compositions include ceria nanoparticles which all have substantially the same size (i.e., are monodisperse or uniform) as well as having varying sizes (i.e., are polydisperse).

In some embodiments, compositions are formed of colloidal solutions of ceria nanoparticles. The term "colloidal ceria nanoparticles" is used in its conventional sense to refer to solid ceria nanoparticles dispersed though a liquid medium (e.g., water) and include but is not limited to colloidal ceria emulsions or colloidal ceria dispersions. The amount of ceria nanoparticles in the colloid ranges from 5% by weight to 50% by weight, such as 10% by weight to 45% by weight, such as 15% by weight to 40% by weight, such as 20% by weight to 35% by weight and including 25% by weight to 30% by weight. The total mass of ceria nanoparticles in the subject compositions applied per $cm^2$ of electrode area can range from 0.5 to 500 mg/$cm^2$ of ceria nanoparticles, such as 10 mg $cm^2$ to 250 mg $cm^2$, such as 25 to 500 mg $cm^2$, such as 50 to 250 mg $cm^2$, such as 75 to 150 mg $cm^2$ and including 100 mg $cm^2$ of ceria nanoparticles. As such, the weight percentage of ceria nanoparticles in compositions of interest may be 1% by weight or more, such as 2% by weight or more, such as 5% by weight or more, such as 10% by weight or more, such as 15% by weight or more, such as 20% by weight or more, such as 25% by weight or more, such as 30% by weight or more, such as 35% by weight or more and including 50% by weight or more ceria nanoparticles. In some embodiments, the weight percentage of ceria nanoparticles ranges between 1% by weight and 95% by weight, such as between 10% by weight and 80% by weight, including between 20% by weight and 70% by weight.

Where the subject compositions include colloidal ceria nanoparticles, the total dry mass of colloidal ceria nanoparticles applied per $cm^2$ in the composition is an amount such that the final mass of ceria nanoparticles (i.e., without the solvent from the colloid) in the composition ranges from 0.1 to 100 mg $cm^2$, such as 0.5 to 50 mg $cm^2$, such as 1 to 10 mg $cm^2$, such as 0.5 to 2.5 mg $cm^2$, such as 0.75 to 1.5 mg $cm^2$ and including 1 mg to 2 mg $cm^2$ of ceria nanoparticles. For example, where the colloid is 50% by weight ceria nanoparticles, the applied composition mass per $cm^2$ may be from 0.2 mg to 100 mg $cm^2$ of the colloidal ceria nanoparticles.

Aspects of the disclosure include compositions having ceria nanoparticles for employing in an electrochemical test strip, such as for example that have a ceria nanoparticle composition-cathode and/or ceria nanoparticle composition-reference electrode. In some embodiments, ceria nanoparticle compositions are operably associated with one or more conductive materials to form an in vitro analyte sensor, for example may be layered with or mixed with a conductive material(s). A conductive material used may be any suitable electrical conductor, including but not limited to gold, carbon, platinum or other platinum group metal, platinum-carbon, doped-tin oxide, indium tin oxide, ruthenium, ruthenium dioxide, palladium, silver, nickel, rhodium, cobalt, titanium as well as conductive polymers, described in greater detail below, and combinations thereof. In some embodiments, the conductive material is conductive carbon.

Conductive carbon, such as a carbon black, may be formed of branched chain-forming particles having diameters smaller than 50 nm, such as 20 nm, such as 10 nm, such as 5 nm and including a diameter smaller than 2 nm. The carbon can be treated by exposure to plasma in the presence of oxygen or air at reduced pressure (e.g., 0.2 to 10 Torr) to improve wetting or to allow suspension of the carbon particles in water.

The amount of conductive material mixed with the compositions of interest may vary, depending on the size of the electrode, the amount of ceria nanoparticles and desired properties of the electrode. For example, the amount of conductive material mixed with the composition to form a reference electrode may range from 0.1 mg to 100 mg, such as 0.1 mg to 10 mg, whereas the amount of conductive material mixed with the composition to form within a cathode may range from 5 to 1000 mg, such as 10 mg to 750 mg, such as 25 mg to 500 mg, such as 50 to 250 mg, such as 75 mg to 150 mg and including 100 mg of conductive material. As such, the weight percent of conductive material in compositions of interest may be 1% by weight or more, such as 2% by weight or more, such as 5% by weight or more, such as 10% by weight or more, such as 15% by weight or more, such as 20% by weight or more, such as 25% by weight or more, such as 30% by weight or more, such as 35% by weight or more, such as 50% by weight or more and including 60% by weight or more conductive material.

The weight ratio of ceria nanoparticles to conductive material in a composition may range from 1:1 and 1:2.5; 1:2.5 and 1:5; 1:5 and 1:10; 1:10 and 1:25; 1:25 and 1:50; 1:50 and 1:100 or a range thereof. For example, the weight ratio of ceria nanoparticles to conductive material in ceria nanoparticle compositions may range between 1:1 and 1:10; 1:5 and 1:25; 1:10 and 1:50; or 1:25 and 1:100. Alternatively, the weight ratio of conductive material to ceria nanoparticles in the composition may range from between 1:1 and 1:2.5; 1:2.5 and 1:5; 1:5 and 1:10; 1:10 and 1:25; 1:25 and 1:50; 1:50 and 1:100 or a range thereof. For example, the weight ratio of conductive material to ceria nanoparticles in compositions of interest may range between 1:1 and 1:10; 1:5 and 1:25; 1:10 and 1:50; or 1:25 and 1:100.

For their application to surfaces the compositions can further include one or more inorganic or organic acids, part or all of which may be removed upon drying. The inorganic acid can be for example hydrochloric acid. The organic acid may be any suitable organic acid, such as acetic acid or a halogenated (e.g., fluorinated) organic acid, including but not limited to trifluoroacetic acid (TFA), perfluorooctanoic acid (PFOA), heptafluorobutyric acid, trifluorobutyric acid, trifluoropropionic acid, combinations thereof, among other organic acids. The concentration of the inorganic or organic acid in the ceria nanoparticle compositions before drying may vary, depending on the amount of conductive material and ceria nanoparticles. For example, the concentration of organic acid may range from 0.01 w/v % to 1 w/v %, such as 0.05 w/v % to 1 w/v %, such as 0.1 w/v % to 0.9 w/v %, such as 0.15 w/v % to 0.75 w/v %, such as 0.2 w/v % to 0.6 w/v %, including 0.1 w/v % to 0.5 w/v %.

The weight ratio of inorganic or organic acid to ceria nanoparticles in compositions of interest, before drying, may range between 1:1 and 1:10; 1:5 and 1:25; 1:10 and 1:50; or 1:25 and 1:100; 1:50 and 1:500; or 1:100 and 1:1000.

Compositions of interest may further include one or more organic polymers. The polymers can be uncharged, polyanionic, polycationic or poly-zwitterionic. For example, the polymer may be a heterocyclic-nitrogen containing water-soluble or hydrophilic polymer or a water wetted or water swellable polymer. Polymers of interest may also be crosslinked, such as with two or more glycidyl moieties. Suitable polymers may include polymers which are water soluble prior to crosslinking and may swell in the presence of water, but do not substantially dissolve in water after their crosslinking or curing. The subject polymers may include, for example, primary, secondary, tertiary or quaternary amine functions, aliphatic amine groups, (such as for example, polyethyleneimine, polyallylamine or polymethacryloxyethyltrimethylammonium salts, e.g. bromide or chloride salts) or heterocyclic nitrogen-containing groups (e.g., poly-N-vinylimidazole, poly-2 or 4-vinylpyridine or partially N-alkylated ammonium salts of poly-2 or 4-vinylpyridine or poly-glucosamine like chitosan). Organic polymers of the present disclosure may be conductive polymers, such as polycationic polymers or polyanionic polymers (e.g., polymers having sulfonic acid and/or carboxylic acid or other ionizable acidic moieties). Organic polymers of the present disclosure may further include a crosslinking agent, such as for example a glycidyl crosslinker (e.g., polyethyleneglycol diglycidyl ether, PEGDGE).

The amount of organic polymer in compositions of interest may vary, depending on the size of the electrode, the amount of ceria nanoparticles and desired properties of the electrode. For example, the amount of organic polymer applied per $cm^2$ of electrode area may range from 1 to 500 mg $cm^{-2}$, such as 10 mg to 250 mg $cm^{-2}$, such as 25 to 500 mg $cm^{-2}$, such as 50 to 250 mg $cm^{-2}$, such as 75 to 150 mg $cm^{-2}$ and including 100 mg $cm^{-2}$ of organic polymer. As such, the weight percentage of organic polymer in dry compositions of interest may be 1% by weight or more, such as 2% by weight or more, such as 5% by weight or more, such as 10% by weight or more, such as 15% by weight or more, such as 20% by weight or more, such as 25% by weight or more, such as 30% by weight or more, such as 35% by weight or more and including 50% by weight or more. In some embodiments the weight percentage of the organic polymer in the composition ranges between 1% to 50% by weight, such as 1% to 5% by weight, such as 5% to 10% by weight, such as 10% to 20% by weight, such as 20% to 30% by weight, such as 30% to 40% by weight, and including 40% to 50% by weight.

The weight ratio of organic polymer to ceria nanoparticles in the composition may range between 1:1 and 1:2.5; 1:2.5 and 1:5; 1:5 and 1:10; 1:10 and 1:25; 1:25 and 1:50; 1:50 and 1:100 or a range thereof.

Ceria nanoparticle compositions of interest may further include one or more binders. The binder may be cured to further bind the conductive material and ceria nanoparticles together in the composition. In certain instances, curing the binder increases the conductivity of the composition. By "increases the conductivity" is meant that a composition where the binder is cured has a conductivity which is greater than if the binder were not present and/or uncured. Increased conductivity may be 10% greater than a composition having the same binder but is left uncured, such as 25% greater, such as 50% greater, such as 75% greater and including a conductivity which 100% greater than the conductivity of a composition having the same binder but is left uncured.

Suitable binders, such as elastomeric binders, which may include, but are not limited to a water wetted polyurethane resins, cellulose derivatives, and highly fluorinated polymers. These binders may be cured using, for example, heat or light, including ultraviolet (UV) light. The appropriate curing method typically depends on the particular binder which is used. Other suitable binders may include but are not limited to smaller molecules like a diamine, triamine, tetramine or polyamine such as 1,2-diaminopropane crosslinked, for example, with water soluble diepoxides or triepoxides.

The amount of binder in the composition varies depending on the amount of ceria nanoparticles and conductive material in a given composition. The weight percent of binders in subject compositions may be 1% by weight or more, such as 2% by weight or more, such as 5% by weight or more, such as 10% by weight or more, such as 15% by weight or more, such as 20% by weight or more and including 25% by weight or more binder.

The weight ratio of binder to ceria nanoparticles in the composition can range between 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof. For example, the weight ratio of binder to ceria nanoparticles in the composition may range between 1:1 and 1:10; 1:5 and 1:25; 1:10 and 1:50; or 1:25 and 1:100; 1:50 and 1:500; or 1:100 and 1:1000.

In certain embodiments, compositions may include one or more polyanionic or polycationic polymers. The polyanionic polymer may be any suitable negatively charged polymer, such as a polymer comprising sulfonic acid or carboxylic acid functions, exemplified by polystyrene sulfonic acid and polyacrylic acid. The polycationic polymer may be any suitable positively charged polymer, including but not limited to polyallylamine, chitosan, poly-2-vinylpyridine, poly-2-vinyl-N-methylpyridinium hydroxide, poly-4-vinylpyridine, poly-4-vinyl-N-methylpyridinium hydroxide, poly-2-vinylpyridine-N-oxide, poly-2-vinylpyridine-N-hydroxide, poly-N-vinylimidazole and poly-4-vinylpyrdine co-polyethylene oxide, un-cross-linked and di-, tri- or poly-epoxide cross-linked polyamines, cationic polyacrylates and polymethacrylates or combinations thereof.

The amount of anionic or cationic polymer in the composition varies depending on the amount of ceria nanoparticles and conductive material in a given composition. The weight percent of cationic polymer in subject compositions may be 1% by weight or more, such as 2% by weight or more, such as 5% by weight or more, such as 10% by weight or more, such as 15% by weight or more, such as 20% by weight or more and including 25% by weight or more cationic polymer. As such, the total amount of anionic or cationic polymer per $cm^2$ in a given composition may range from 0.5 to 250 mg $cm^{-2}$, such as 10 mg to 75 mg $cm^{-2}$, such as 25 to 50 mg $cm^{-2}$, such as 50 to 250 mg $cm^{-2}$, such as 75 to 150 mg $cm^{-2}$ and including 100 mg $cm^{-2}$.

The weight ratio of anionic or cationic polymer to ceria nanoparticles in the composition ranges from 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof. For example, the weight ratio of anionic or cationic polymer to ceria nanoparticles may range between 1:1 and 1:10; 1:5 and 1:25; 1:10 and 1:50; 1:25 and 1:100; 1:50 and 1:500; or 1:100 and 1:1000.

Compositions of interest may further include one or more surfactants, such as for example a cationic surfactant. The term "cationic surfactant" is used in its conventional sense to refer to surfactants having a positively charged head group. Cationic surfactants of interest may include, but are not limited to a cetyltrimethylammonium halide like bromide (CTAB), hexadecyltrimethylammonium halide like bromide (HTAB), lauryl amido propyl trimethyl ammonium halide or methosulphate, undecyl amido propyl trimethyl ammonium halide or methosulphate, polyglycolether, quaternary ammonium salts, quaternary ammonium compounds which can be based on polyoxyethylene alkyl and alicyclic amines or combinations thereof. The amount of surfactant in the composition varies depending on the amount of ceria nanoparticles and conductive material in a given composition. The weight percent of surfactants in subject compositions may be 0.1% by weight or more, such as 0.2% by weight or more, such as 0.5% by weight or more and including 1% or more. As such, the total amount of surfactant per $cm^{-2}$ in a given composition may range from 0.05 to 100 mg $cm^{-2}$, such as 0.1 to 75 mg $cm^{-2}$, such as 0.25 to 50 mg $cm^{-2}$, such as 5 to 25 mg $cm^{-2}$, such as 7.5 mg to 15 mg $cm^{-2}$ and including 10 mg $cm^{-2}$.

Where both a surfactant and binder are included, the molar ratio of cationic surfactant to binder in the composition ranges from 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof. For example, the molar ratio of cationic surfactant to polycationic binder in compositions of interest may range between 1:1 and 1:10; 1:5 and 1:25; 1:10 and 1:50; 1:25 and 1:100; 1:50 and 1:500; or 1:100 and 1:1000. In other embodiments, the molar ratio of polycationic binder to cationic surfactant in the composition ranges between 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof. For example, the ratio of polycationic surfactant to cationic binder in compositions of interest may range between 1:1 and 1:10; 1:5 and 1:25; 1:10 and 1:50; or 1:25 and 1:100; 1:50 and 1:500; or 1:100 and 1:1000.

Ceria nanoparticles compositions according to certain embodiments are rapidly water-wetted compositions. By "rapidly water-wetted" is meant that a drop of water applied to the surface can spread and wet about the entire surface of an electrode in about 2 seconds or less, for example in less than 1 second. Rapidly water wetted compositions are referred to herein as "water wetted". When a drop of water placed on a surface of water wetted composition, the contact angle of the drop can be 10° or less, such as for example 5° or less. Rapid wetting and spreading are important because if wetting is slow or incomplete, it can take an inconveniently long time, for example 20 s or longer, or 30 s or longer or longer than 1 min to complete the assay of the chemical or biochemical, for example using a coulometric strip where accuracy requires filling of a chamber of an electrochemical cell having a wall coated by the composition.

Although the above compositions have been specifically described with ceria nanoparticles, the subject compositions may alternatively include nanoparticles of any lanthanide oxide or actinide oxide or a combination thereof. The term "lanthanide" is used in its conventional sense to refer to the fifteen chemical elements having atomic numbers from 57 to 71. As such, lanthanide oxides of the present disclosure include mixed valence oxides of the elements cerium, praseodymium, samarium, terbium, dysprosium, holmium and erbium. Similarly, the term "actinide" is used in its conventional sense to refer to the less radioactive and long lived mixed valence oxides of thorium, and uranium.

Ceria Nanoparticle Cathodes

Aspects of the present disclosure also include cathodes having one or more of the subject ceria nanoparticle compositions. In certain embodiments, an amount of ceria nanoparticle composition is deposited on surface of a conductive material (e.g., layered over the conductive material) to form a cathode. The conductive material may be deposited over an inert non-conducting substrate or the conductive material may itself provide the structural support of an electrode that can be, for example, planar or have, for example, the form of a needle or a wire. In other embodiments, an amount of ceria nanoparticle composition is combined with a conductive material to form a cathode, for example mixed with the conductive material to provide a conductive ceria nanoparticle composition. The conductive ceria nanoparticle composition may alternatively be formed or shaved to provide the structural support to act as an electrode while in use, such as, for example, a needle or a wire. Both a conductive layer and a conductive ceria nanoparticle composition may be used in a single electrode or plurality of electrodes of a single sensor, in certain instances.

The cathode can have a variety of forms and can be made from a variety of materials. For example, the cathode can be planar, formed for example as a plate, or have the form of a mesh, tube, wire, or have another shape. A cathode may be planar as well as non-planar, and an exterior surface, an interior surface, or a combination of exterior and interior surfaces, may be designed to be fluidic contact with the biological fluid when the cathode is positioned in vivo.

The ceria nanoparticle composition may be applied to a surface of a substrate by a variety of methods, including, for example hot or cold spraying, drop casting, spin casting, sputtering, doctor blading, printed on a flat surface, or printed in an embossed or otherwise recessed surface, transferred from a separate carrier or liner, etched, or molded physical vapor deposition, plasma deposition, chemical vapor deposition and printing among other deposition methods. Suitable methods of printing include screen-printing, piezoelectric printing, ink jet printing, laser printing, photolithography, painting, gravure roll printing, transfer printing, and other known printing methods.

The cathode substrate may be any suitable size, as desired, having a length which ranges from 0.1 mm to 5.0 mm, such as from 0.5 mm to 4.5 mm, such as from 1.0 mm to 4.0 mm, such as from 1.5 mm to 3.0 mm and including 2.5 mm and a width which ranges from 0.1 mm to 5.0 mm, such as from 0.5 mm to 4.5 mm, such as from 1.0 mm to 4.0 mm, such as from 1.5 mm to 3.0 mm and including 2.5 mm. A cathode width may be uniform along its entire length or may vary. Shorter or longer lengths and narrower or wider widths may also suitable. The geometric area of the cathode substrate may range from 0.1 $mm^2$ to 50 $mm^2$, such as from 10 $mm^2$ to 25 $mm^2$, such as from 10 $mm^2$ to 20 $mm^2$, such as from 10 $mm^2$ to 10 $mm^2$ and including 5 $mm^2$. The cathodes can operate in a biological fluid providing, for example, a current density greater than 0.2 mA $cm^{-2}$ when poised at a potential of about −0.2 V versus the potential of the Ag/AgCl (3 M KCl) electrode. For example, they can provide a current density greater than 0.5 mA $cm^{-2}$, or greater than 1 mA $cm^{-2}$, or greater than 1.5 mA $cm^{-2}$ when poised at a potential of about −0.2 V versus the potential of the Ag/AgCl (3 M KCl) electrode. In analyte monitoring strips the currents of the anode and the cathode are about the same, and the current density of the cathode depends on the current of the anode and the area of the cathode.

The current of the anodes, and therefore of the cathode, typically depends on the analyte concentrations. During the brief time of operation of an exemplary blood glucose monitoring strip, typically less than about 20 seconds, the mean cathode current density at 20 mM glucose concentration or higher can be greater than 0.5 mA $cm^{-2}$ and for 6 seconds it can it can be greater than 1 mA $cm^{-2}$. For a 10 mm² cathode the mean current can be greater than 0.1 mA for 6 s and it can be greater than 50 µA for 20 s. For a 20 mm² cathode the mean current can be greater than 0.2 mA for 6 s and it can be greater than 0.1 mA for 20 s. In general, the strips and their cathodes operate at temperatures between about 25° C. and about 45° C.

In certain embodiments in which an inert substrate is used, the substrate is a non-conducting material, such as for example polymeric, plastic, glass, silicon-containing materials, dielectric materials, or ceramic materials, among other non-conducting materials. The substrate may be a flexible, deformable or thermoplastic substrate of polycarbonate, polyester (e.g., polyethylene terephthalate (PET)), polyvinyl chloride (PVC), polyurethane, polyether, polyamide, polyimide, combinations or copolymers thereof, such as glycol-modified polyethylene terephthalate. Alternatively, the substrate may be a rigid substrate to, for example, provide structural support against bending or breaking Examples of rigid materials that may be used as the substrate include low conductivity ceramics, such as aluminum oxide and silicon dioxide. A substrate may also have a varying rigidity along a dimension, e.g., length and/or width, of the substrate. In certain embodiments, the conductive ceria nanoparticles layer may be deposited onto a porous or microporous substrate. For example, the substrate may be formed, for example, as a mesh, a reticulated structure (e.g., reticulated graphite), a microporous film, or a film that is permeable to an analyte of interest. Likewise, the surface area of the substrate may further be increased by roughening. Where the surface of the cathode is roughened, the exposed surface area of the cathode may be greater than the geometric surface area to which the conductive ceria nanoparticles composition is applied. For example, the exposed surface area of a cathode which is roughened may be 2-fold or greater than the geometric surface area to which the ceria nanoparticle composition is applied, such as 3-fold or greater, such as 5-fold or greater, such as 10-fold or greater and including 25-fold or greater than the geometric surface area to which the ceria nanoparticle composition is applied.

As described above, in certain embodiments, the ceria nanoparticle composition is combined with a conductive material to provide a conductive ceria nanoparticle composition for use as a cathode. For example, the ceria nanoparticle composition may be mixed with gold, carbon, platinum or other platinum group metal, platinum-carbon, doped-tin oxide, indium tin oxide, ruthenium, ruthenium dioxide, palladium, silver, copper, nickel, rhodium, cobalt, titanium and combinations thereof. The mixtures can be heterogeneous or homogenous, where homogenous may be desired when used as an electrochemical sensor cathode.

In certain embodiments, the cathode substrate may be a non-corroding conductive substrate, such as a plate, or a needle, or a wire. In some instances, the conductive substrate is a non-conductive substrate which has a conductive coating on the surface of the non-conductive substrate. Suitable conductive substrate and/or conductive coatings may include, but are not limited to gold, carbon, platinum or other platinum group metal, platinum-carbon, doped-tin oxide, indium tin oxide, ruthenium, ruthenium dioxide, palladium, silver, nickel, rhodium, cobalt, titanium and combinations thereof. Alternatively, the non-conducting cathode substrate may include a conductive polymer coating. Suitable conductive polymeric coatings include, but are not limited to, conductive organic polymers, such as PEDOT (poly(3,4-ethylenedioxythiophene) or conductive polymers and copolymers of thiophene or its derivatives, or pyrrole or its derivatives, or acetylene. The organic polymer coatings can, in some embodiments, be polycationic. Where the substrate is a conductive substrate (e.g., a conductive wire or needle), the ceria nanoparticle compositions may or may not further include a conductive material, depending on the desired conductivity of the resulting cathode. A cathode may include a plurality of conductive and nonconductive layers, where all of the materials may be the same or at least some may be different.

The ceria nanoparticle composition may be applied to at least a portion of one or more surfaces of a substrate to form a cathode. In some embodiments, the ceria nanoparticle composition is applied to at least a portion of at least 1 surface of the substrate. In other embodiments, the ceria nanoparticle composition is applied to 2 or more surfaces of the substrate. Compositions may be applied to at least a portion of all exposed surfaces of a substrate. In certain embodiments, where the substrate is a planar substrate, ceria nanoparticle composition may be applied to all surfaces of the substrate to form the cathode.

As described above, the ceria nanoparticle composition may be applied to part or all of a surface of a substrate to form a cathode. In some embodiments, the ceria nanoparticle composition is applied to an entire surface of the substrate. In other embodiments, less than an entire surface of the substrate is applied with the ceria nanoparticle composition, such as 95% or less of the surface of the substrate is applied with the ceria nanoparticle composition, such as 75% or less, such as 50% or less, such as 25% or less, such as 10% or less, and including 5% or less, including 0.5%, of the surface of the substrate is applied with the ceria nanoparticle composition.

In certain embodiments, the overall length of the applied area may be no less than 0.01 mm and no greater than 5.0 mm. For example, the length may be between 0.05 mm and 4.5 mm, such as 0.1 mm to 4.0 mm, such as 0.15 mm to 3.0 mm and including 0.25 mm. It is understood, however that shorter and longer deposition areas may also suitable. In certain embodiments, the overall width of the applied area may be no less than 0.01 mm and no greater than 2.5 mm. For example, the width may be between 0.025 mm and 2.0 mm, such as 0.05 mm and 1.5 mm, such as 0.075 mm and 1.0 mm, including 0.1 mm. As such, the area of the cathode covered by the applied conductive ceria nanoparticle composition ranges from 0.0001 mm² to 12.5 mm², such as from 0.001 mm² to 10.0 mm², such as from 0.001 mm² to 9.0 mm², such as from 0.01 mm² to 7.5 mm² and including from 0.1 mm² to 5.0 mm².

As such, the geometrical areas of cathodes having the ceria nanoparticle composition may be between about 0.02 mm² and about 10 mm², for example between about 0.05 mm² and 5 mm² or between about 0.1 mm² and about 2 mm². The current densities of the cathodes may range from about 0.05 µA cm$^{-2}$ mM$^{-1}$ and about 50 µA cm$^{-2}$ mM$^{-1}$, such as from about 0.1 µA cm$^{-2}$ mM$^{-1}$ and about 20 µA cm$^{-2}$ mM$^{-1}$.

The conductive compositions may be applied to a surface of a substrate within an ink, such as a printing ink. Depending on the concentration of each component in the ceria nanoparticle composition, the dry volume of the composition employed per cm² to produce a cathode may vary and may range from 1 µL to 250 µL, such as from 2 µL to 200 µL, such as 5 µL to 150 µL, such as from 10 µL to 125 µL, such as from 15 µL to 100 µL, such as from 20 µL to 75 µL and including from 25 µL to 50 µL. When applied within an ink or by any other means in order to produce a cathode, the mass of ceria nanoparticles employed per cm² can range from as 0.3 to 500 mg cm$^{-2}$, such as 5 to 500 mg cm$^{-2}$, such as 10 mg to 250 mg cm$^{-2}$, such as 25 mg to 200 mg cm$^{-2}$, such as 50 to 150 mg cm$^{-2}$, such as 0.5 to 200 mg cm$^{-2}$ and including 100 mg cm$^{-2}$.

The density of ceria nanoparticles on the cathode substrate may depend, in some instances on the physical properties of the composition, such as for example diameter of the ceria nanoparticles, the oxygen loading of the ceria nanoparticles and the concentration of ceria nanoparticles in the composition applied to the surface in order to form a cathode. In certain aspects, the area of the substrate on which the conductive ceria nanoparticles composition is applied includes between $10^2$ and $10^{15}$ ceria nanoparticles per mm$^2$. For example, the area of the substrate may include between $10^3$ and $10^{12}$ ceria nanoparticles per mm$^2$, between $10^4$ and $10^{10}$ ceria nanoparticles per mm$^2$, between $10^5$ and $10^8$ ceria nanoparticles per mm$^2$, including between $10^6$ and $10^7$ ceria nanoparticles per mm$^2$.

The average thickness of the layer of ceria nanoparticles composition of the cathode will depend on the number of layers applied as well as the amount of ceria nanoparticle composition employed. For example, one or more layers of the ceria nanoparticle composition may be applied to a substrate to form a cathode, such as two or more layers, such as three or more layers, such as 5 or more layers, and including 10 or more layers of the ceria nanoparticle composition may be applied to a substrate to form a cathode. The thickness of each layer may be the same or different, as desired. For example, where the thickness of each layer is different, the thickness of each layer of applied ceria nanoparticle composition may differ by 75% or less, such as 50% or less, such as 40% or less, such as 30% or less, such as 25% or less and including by 10% or less. Accordingly, the total thickness of the applied composition may be 1 µm or more, such as 5 µm or more, such as 10 µm or more, such as 15 µm or more, such as 20 µm or more, such as 50 µm or more, including 100 µm or more. Additional layers of ceria nanoparticle composition may be added if necessary, such as for example to increase the coulombic capacity and/or improve smoothness and uniformity of the ceria nanoparticle layer. For example, if after evaluating the deposited ceria nanoparticle layer it is determined that the thickness of the ceria nanoparticle layer is less than targeted or is unsuitable, additional layers may be applied to all or part of the deposited ceria nanoparticle layer.

The total mass of applied ceria nanoparticles in each layer may vary depending on the size of the applied area on the cathode substrate as well as the number of layers applied. In certain instances, the total mass of ceria nanoparticles applied in each layer may be 10 mg or more, such as 25 mg or more, such as 50 mg or more, such as 75 mg or more, and including 100 mg or more. The density of ceria nanoparticles applied onto the substrate may be adjusted to achieve a desired mass per unit area i.e., loading of ceria nanoparticles on the substrate upon drying of the ceria nanoparticle composition. For example, the ceria nanoparticle number density may be chosen to achieve uniform distribution on the surface of the cathode, and also to provide less than a single layer of ceria nanoparticles on the surface of the substrate. In other embodiments, the ceria nanoparticle density may be chosen to achieve a particular oxygen loading on the cathode surface. In yet other embodiments, the ceria nanoparticle surface-density may be chosen to achieve 50% or greater coverage of the surface of the substrate, such as 75% or greater, such as 80% or greater, such as 85% or greater, such as 90% or greater, such as 95% or greater and including 99% or greater coverage of the surface of the cathode.

Cathodes employing the ceria nanoparticle compositions according to the present disclosure include an amount of absorbed oxygen loaded into the ceria nanoparticles, as described above. The amount of absorbed oxygen loaded into the nanoparticles may vary depending on the source of ceria, the number of lattice vacancies as well as the desired properties of the ceria nanoparticles. Absorbed oxygen can be, for example, molecular oxygen (i.e., $O_2$), bound superoxide radical anion (i.e., $.O_2^-$) or superoxide radical (.OOH). The amount of absorbed oxygen loaded into the subject ceria nanoparticles when employed in a cathode may be 0.1 percent by weight or more, such as 0.2 percent by weight or more, such as 0.3 percent by weight or more, such as 0.5 percent by weight or more, such as 1.0 percent by weight or more, such as 1.5 percent by weight or more and including a molecular oxygen loading of 2.5 percent by weight or more.

The total coulombic capacity of cathodes employing the ceria nanoparticle compositions is typically 0.5 millicoulombs (mC) or greater, such as 2 mC or greater, such as 5 mC or greater and including 10 mC or greater. The coulombic capacity per cm$^2$ of cathodes employing the ceria nanoparticle compositions is 0.5 mC cm$^{-2}$ or greater, such as 1 mC cm$^{-2}$ or greater, such as 5 mC cm$^{-2}$ or greater, 10 mC cm$^{-2}$ or greater, such as 20 mC cm$^{-2}$ or greater, and including 50 mC cm$^{-2}$ or greater, e.g. 0.1 C cm$^{-2}$ or greater. As such, this electroreducible oxidant provides for smaller cathodes with higher current density and better retention of linear response.

The ceria nanoparticle composition can be electroreduced while glucose, dissolved in a fluid of the body (e.g., blood, interstitial fluid, etc.) is oxidized or electro-oxidized. The ceria nanoparticle composition can be rapidly electroreduced when the cathode is poised at a potential positive of −0.3 V versus the potential of an Ag/AgCl (3 M KCl) electrode, for example at about −0.2 V versus the potential of an Ag/AgCl (3 M KCl) electrode. At −0.2 V versus the potential of an Ag/AgCl (3 M KCl) electrode the mean Faradaic current density of the cathode can be during the initial 6 seconds of its operation 0.1 mA cm$^{-2}$ or greater, such as 0.2 mA cm$^{-2}$ or greater, 0.5 mA cm$^{-2}$ or greater, including 1 mA cm$^{-2}$ or greater. Furthermore, when the composition is electro-reduced, the mean Faradaic current density of the cathode can be during the initial 20 seconds of its operation 0.1 mA cm$^{-2}$ or greater, such as 0.2 mA cm$^{-2}$ or greater, including 0.5 mA cm$^{-2}$ or greater as seen, for example, in Table 1 of Example 14. The high initial current density at such a potential provides, for example, for rapid coulometric assay of glucose in a strip.

Ceria Nanoparticle Reference Electrodes.

Aspects of the present disclosure also include reference electrodes having one or more of the subject ceria nanoparticle compositions. In certain embodiments, in order to form the reference electrode the ceria nanoparticle composition is deposited on the surface of a conductive material (e.g., layered over the conductive material). In such embodiments, the conductive material may be deposited over an inert non-conducting substrate or over a conductive material coating of an inert non-conductive substrate or on the conductive material which may itself provide the structural support to act as an electrode while in use, such as, for example, a metallic needle or a wire. In some embodiments, in order to form the reference electrode the ceria nanoparticle composition is combined with a conductive material, for example mixed with the conductive material to provide a conductive ceria nanoparticle composition. The conductive ceria nanoparticle composition may alternatively be formed or shaped to provide the structural support to act as a reference electrode while in use, such as, for example, a needle or a wire.

In certain embodiments, the reference electrode includes a cerium nanoparticle composition that includes a mixed valence cerium nanoparticle composition. "Mixed valence" means that the nanoparticle lattices and/or their surfaces include both $Ce^{3+}$ and $Ce^{4+}$ cations, as is the case in oxygen-deficient ceria, $CeO_{2-x}$. The lattice structure of the inner bulk of the mixed valence cerium nanoparticles can be partly, mostly, or entirely similar to that of crystalline, e.g. fluorite structure, ceria ($CeO_2$). Although macrocrystalline ceria is neither electroreduced nor electrooxidized in a neutral pH aqueous solution, for example in neutral pH 0.1 M NaCl, in a potential range within 0.3 V of that of the Ag/AgCl (3M KCl) electrode, $Ce^{4+}$ at or near the surface of the nanoparticles can be electroreduced and $Ce^3$ and/or bound oxygen at or near the surface of the nanoparticles can be electrooxidized. The corresponding electrode potential associated with the reversible electrochemical reaction of the surface or near surface bound ions can differ by less than 0.3 V from that of the Ag/AgCl (3 M KCl) electrode at about 25° C. The potential of the $CeO_{2-x}$ nanoparticles comprising electrode can differ from the potential of the Ag/AgCl (3 M KCl) electrode, for example, by less than 250 mV, or by less than 200 mV, or by less than 150 mV, or by less than 100 mV or by less than about 70 mV.

The amount of ceria nanoparticles applied per $cm^2$ can typically be greater than about 0.01 mg $cm^{-2}$ and can be less than about 100 mg $cm^{-2}$. It can be, for example, more than 0.1 mg $cm^{-2}$ and it can be less than about 10 mg $cm^{-2}$, or for example, it can be more than 0.1 mg $cm^{-2}$ and it can be less than about 2 mg $cm^{-2}$.

Furthermore, the redox potential of the ceria nanoparticle comprising reference electrode can be about independent of pH, for example in the pH range of the analyzed fluids of the body. Additionally, unlike the potential-defining redox reaction of the Ag/AgCl electrode, which is $AgCl+e^- \leftrightarrow Ag+Cl^-$, the redox potential of the ceria nanoparticle comprising reference electrode can also be independent of the concentration of the chloride anion. The redox potential of the reference electrode comprising $CeO_{2-x}$ nanoparticles can be near the potential of the Ag/AgCl (3M KCl) electrode and very close to the potential of an Ag/AgCl in a physiological saline, about 0.1 M NaCl, solution or in blood. The potential of the ceria nanoparticle comprising reference electrode can differ by less than 300 mV from the potential of the Ag/AgCl in the analyzed solution, for example it can differ by 0-300 mV, for example by 0-200 mV, or by 0-100 mV or by 0-60 mV from the potential of the Ag/AgCl (3 KCl) electrode potential. The similarity of potentials can facilitate the substitution of Ag/AgCl (a mixture of Ag and AgCl) in analyte sensors, for example in ex-vivo sensors of glucose and other analytes, such as strips for blood glucose monitoring.

Certain embodiments can optionally include compositions having cerium nanoparticles of the formula $CeO_{2-x}$ where x is 0.1 or greater, such as 0.15 or greater, such as 0.2 or greater, such as 0.25 or greater. Because of charge neutrality, missing oxide anions can be associated with the presence of $Ce^{3+}$ ions, for example at or near the surface of the nanoparticle.

For use in reference electrodes the $CeO_{2-x}$ nanoparticles can be heated to at temperature higher than about 200° C. or 300° C. for example to 400° C., optionally in an about oxygen-free atmosphere. Such heating may cause the nanoparticles to loose $O_2$ and can provide a more precisely defined electrode potential. For example, coating of an electrode with a mixture containing the cerium nanoparticles heated to 400° C., carbon black and polymer can provide an electrode with a potential of about 70 mV versus Ag/AgCl in 3 M KCl.

A reference electrode may be planar as well as non-planar. In some embodiments, the reference electrode includes a layer of the ceria nanoparticle composition applied onto a surface of a substrate, where the substrate may be pre-coated with a non-corroding conductor. The non-corroding conductor can be, or can comprise, a conductive organic polymer such as PEDOT (poly(3,4-ethylenedioxythiophene) or a polymer or copolymer of thiophene or a substituted thiophene, or a polymer or copolymer of pyrrole or a substituted pyrrole, or polyacetylene. The non-corroding conductor can also be carbon or gold.

Furthermore, when the composition comprises also particles of a conductor like carbon, it can be coated directly on an inert, non-conducting base such as a strip, a plate, a tube or a mesh. The ceria nanoparticle composition may be applied to a surface of the substrate by a variety of methods, including, for example, vacuum deposition, drop casting, spin casting, sputtering, printing on a flat surface, printing in an embossed or otherwise recessed surface, transferred from a separate carrier or liner, etched, or molded physical vapor deposition, plasma deposition, chemical vapor deposition among other deposition methods. Suitable methods of printing include screen-printing, piezoelectric printing, ink jet printing, laser printing, photolithography, painting, gravure roll printing, transfer printing, and other known printing methods.

The reference electrode substrate may be any suitable size. It can have typically a length which ranges from 0.01 mm to 5.0 mm, such as from 0.1 mm to 4.5 mm, such as from 1.0 mm to 4.0 mm, such as from 1.5 mm to 3.0 mm and including 2.5 mm and a width which ranges from 0.01 mm to 5.0 mm, such as from 0.1 mm to 4.5 mm, such as from 1.0 mm to 4.0 mm, such as from 1.5 mm to 3.0 mm and including 2.5 mm. It is understood, however that shorter or longer lengths and narrower or wider widths may also suitable. The geometric area of the reference electrode may range from 0.01 $mm^2$ to 25 $mm^2$, such as from 0.1 $mm^2$ to 20 $mm^2$, such as from 1 $mm^2$ to 15.0 $mm^2$, such as from 1.0 $mm^2$ to 10 $mm^2$ and including 5.0 $mm^2$.

In certain embodiments in which an inert substrate is used, the substrate can be a non-conducting material, such as for example polymeric, plastic, glass, silicon-containing or ceramic among other non-conducting materials. Typically it is a plastic strip. In some embodiments, the substrate is a flexible, deformable or thermoplastic substrate of polycarbonate, polyester (e.g., polyethylene terephthalate (PET)), polyvinyl chloride (PVC), polyurethane, polyether, polyamide, polyimide, combinations or copolymers thereof, such as glycol-modified polyethylene terephthalate. In other embodiments, the substrate may be a rigid substrate such as aluminum oxide and silicon dioxide. A substrate may also have a varying rigidity along a dimension of the substrate. In certain embodiments, the ceria nanoparticles layer may be deposited onto a porous or microporous substrate. For example, the substrate may be formed, for example, as a mesh, a reticulated structure, a microporous film, or a film that is permeable to an analyte of interest.

As noted above, in certain embodiments, the ceria nanoparticle composition is combined with a conductive material to provide a conductive ceria nanoparticle composition for use as a reference electrode. For example, the ceria nanoparticle composition may include gold, carbon, platinum or other platinum group metal, platinum-carbon, doped-tin oxide, indium tin oxide, ruthenium, ruthenium dioxide, palladium, silver, nickel, rhodium, cobalt, titanium and combinations thereof.

In other embodiments, the ceria nanoparticle composition is deposited on a conductive substrate to form a reference electrode, such as needle or a wire. In some instances, the conductive substrate is a non-conductive substrate which has a conductive coating on the surface of the non-conductive substrate. Suitable conductive substrate and/or conductive coatings may include, but are not limited to gold, carbon, platinum or other platinum group metal, platinum-carbon, doped-tin oxide, indium tin oxide, ruthenium, ruthenium dioxide, palladium, silver, nickel, rhodium, cobalt, titanium and combinations thereof. Alternatively, the non-conducting reference electrode may include a conductive polymer coating. Suitable conductive polymeric coatings include, but are not limited to conductive organic polymers, such as PEDOT (poly(3,4-ethylenedioxythiophene) or conductive polymers and copolymers of thiophene, or pyrrole, or acetylene that may be polycationic conductive polymers. Where the substrate is a conductive substrate (e.g., a conductive wire or needle), the ceria nanoparticle compositions may or may not further include a conductive material, depending on the desired conductivity of the resulting reference electrode. A reference electrode may include a plurality of conductive and nonconductive layers, where all of the materials may be the same or at least some may be different.

The conductive ceria nanoparticle composition may be applied to one or more surfaces of a substrate to form a reference electrode. In some embodiments, the ceria nanoparticle composition is applied to at least a portion of at least 1 surface of the substrate. In other embodiments, the ceria nanoparticle composition is applied to 2 or more surfaces of the substrate, such as 3 or more surfaces of the substrate, such as 4 or more surfaces of the reference electrode substrate and including 5 or more surfaces of the substrate. In certain embodiments, where the reference electrode substrate is a planar substrate, ceria nanoparticle composition may be applied to all surfaces of the substrate to form the reference electrode.

The ceria nanoparticle composition may be applied to part or all of a surface of a substrate to form a reference electrode. In some embodiments, the ceria nanoparticle composition is applied to an entire surface of the substrate. In other embodiments, less than an entire surface of the substrate is applied with the ceria nanoparticle composition, such as 95% or less of the surface of the substrate is applied with the conductive ceria nanoparticle composition, such as 75% or less, such as 50% or less, such as 25% or less, such as 10% or less, and including 5% or less, including 0.5%, of the surface of the substrate is applied with the ceria nanoparticle composition.

In certain embodiments, the overall length of the applied area may be no less than 0.01 mm and no greater than 5.0 mm. For example, the length may be between 0.05 mm and 4.5 mm, such as 0.1 mm to 4.0 mm, such as 0.15 mm to 3.0 mm and including 0.25 mm. It is understood, however that shorter and longer deposition areas may also suitable. In certain embodiments, the overall width of the applied area may be no less than 0.01 mm and no greater than 2.5 mm. For example, the width may be between 0.025 mm and 2.0 mm, such as 0.05 mm and 1.5 mm, such as 0.075 mm and 1.0 mm, including 0.1 mm. As such, the area of the reference electrode covered by the applied ceria nanoparticle composition ranges from 0.0001 $mm^2$ to 12.5 $mm^2$, such as from 0.001 $mm^2$ to 10.0 $mm^2$, such as from 0.001 $mm^2$ to 9.0 $mm^2$, such as from 0.01 $mm^2$ to 7.5 $mm^2$ and including from 0.1 $mm^2$ to 5.0 $mm^2$.

When applied to a surface as an ink, for example a printing ink, then depending on the concentration of each component in the ceria nanoparticle composition, the amount of composition employed to produce a reference electrode may vary, and may range after the ink dries from 0.1 µL to 25 µL of the ceria nanoparticle composition, such as from 0.2 µL to 20 µL, such as 0.5 µL to 15 µL, such as from 1 µL to 12.5 µL, such as from 1.5 µL to 10 µL, such as from 2.0 µL to 7.5 µL and including from 2.5 µL to 5.0 µL of the ceria nanoparticle composition. As such, the total mass of ceria nanoparticles applied to the reference electrode substrate varies, ranging from 0.1 to 100 mg of ceria nanoparticles, such as 0.5 mg to 75 mg, such as 2.5 mg to 50 mg, such as 5.0 to 25 mg, such as 7.5 mg to 15 mg and including 10 mg of ceria nanoparticles. Accordingly, the loading of ceria nanoparticles on the reference electrode substrate may range from 0.1 $mg/cm^2$ to 100 $mg/cm^2$, such as from 0.5 $mg/cm^2$ to 20 $mg/cm^2$, such as from 0.75 $mg/cm^2$ to 10 $mg/cm^2$, such as from 1 $mg/cm^2$ to 6.5 $mg/cm^2$ and including from 1.5 $mg/cm^2$ to 5 $mg/cm^2$.

The density of ceria nanoparticles on the substrate may depend in some instances on the physical properties of the composition, such as for example diameter of the ceria nanoparticles and the concentration of ceria nanoparticles in the composition applied to the surface to form a reference electrode. In certain aspects, the area of the substrate on which the ceria nanoparticles composition is applied includes between $10^2$ and $10^{15}$ ceria nanoparticles per $mm^2$. For example, the area of the substrate may include between $10^3$ and $10^{12}$ ceria nanoparticles per $mm^2$, between $10^4$ and $10^{10}$ ceria nanoparticles per $mm^2$, between $10^5$ and $10^8$ ceria nanoparticles per $mm^2$, including between $10^6$ and $10^7$ ceria nanoparticles per $mm^2$.

The average thickness of the layer of ceria nanoparticles composition on the substrate will depend on the number of layers applied as well as the amount of ceria nanoparticle composition applied to the surface per layer. In some embodiments, one or more layers of the ceria nanoparticle composition is applied to the substrate, such as two or more layers, such as three or more layers, such as 5 or more layers, and including 10 or more layers of the ceria nanoparticle composition are applied to the substrate. The thickness of each layer may be the same or different, as desired. For example, where the thickness of each layer is different, the thickness of each layer of applied ceria nanoparticle composition may differ by 75% or less, such as 50% or less, such as 40% or less, such as 30% or less, such as 25% or less and including by 10% or less. Accordingly, the total thickness of the applied composition may be 0.1 µm or more, such as 0.5 µm or more, such as 1.0 µm or more, such as 1.5 µm or more, such as 2.0 µm or more, such as 5 µm or more, such as 10 µm or more, including 100 µm or more. Additional layers of ceria nanoparticle composition may be added to the substrate if necessary, such as for example to improve smoothness and uniformity of the conductive ceria nanoparticle layer. For example, if after evaluating the deposited ceria nanoparticle layer, it is determined that the ceria nanoparticle layer is less than targeted or is unsuitable, additional layers may be applied to all or part of the deposited ceria nanoparticle layer.

Accordingly, the total mass of applied ceria nanoparticles in each layer will vary depending on the size of the applied area on the substrate as well as the number of layers applied. In certain instances, the total mass of ceria nanoparticles applied in each layer is 1 mg or more, such as 10 mg or more, such as 25 mg or more, such as 50 mg or more, such as 75 mg or more, and including 100 mg or more. It will be appreciated that the number density of ceria nanoparticles applied onto the reference electrode may be adjusted to achieve a desired mass per unit area of ceria nanoparticles on the reference electrode upon drying of the ceria nanoparticle composition. For example, the ceria nanoparticle number density may be chosen to achieve uniform distribution on the surface of the reference electrode, and also to provide less than a single layer of ceria nanoparticles on the surface of the substrate. In other embodiments, the ceria nanoparticle density may be chosen to achieve a particular redox potential of the reference electrode.

Ceria Nanoparticle Electrochemical Analyte Test Strips

Aspects of the present disclosure also include electrochemical test strips employing a cathode or reference electrode employing one or more of the subject ceria nanoparticle compositions, such as in vitro analyte test strips. In vitro sensors are also referred to as ex-vivo or discrete sensors in that they operate outside of the body and are never inserted into the body and they only provide analyte information at a discrete or signal point of time when the sample is applied to the sensor, as opposed to in vivo sensors which are positioned within the body for testing and automatically determine analyte information over a period of time. The in vitro electrochemical analyte sensors can be in the form of a strip, and therefore may be referred to as test strips, and the like.

The particular configuration of electrochemical test strips having one or more of a reference electrode and a cathode employing the subject ceria nanoparticle compositions may depend on the use for which the electrochemical test strip is intended and the conditions under which the electrochemical test strip will operate. Electrochemical test strips according to certain embodiments include an in vitro test strip in which a biological sample having an analyte or suspected of having an analyte is removed from the body and is applied to the test strip and the presence and/or concentration of one or more analytes is determined.

A variety of analytes can be detected and quantified using the analyte test strips disclosed herein including, but not limited to, a biochemical like glucose, blood β-ketone, ketone bodies, lactate, acetyl choline, amylase, bilirubin, cholesterol, chorionic gonadotropin, creatine kinase (e.g., CK-MB), creatine, DNA, fructosamine, glutamine, growth hormones, hormones, ketones, lactate, peroxide, prostate-specific antigen, prothrombin, RNA, thyroid stimulating hormone, and troponin, in sample of body fluid and to chemicals like $O_2$, $CO_2$, pH, electrolytes, including chloride anion and potassium cation. Analyte test strips may also be configured to detect and/or quantify drugs, such as, for example, antibiotics (e.g., gentamicin, vancomycin, and the like), digitoxin, digoxin, drugs of abuse, theophylline, and warfarin. In certain embodiments, the analyte test strips of the present disclosure are glucose test strips. The biochemicals are typically coulometrically, amperometrically, chronoamperometrically monitored. The chemicals are often potentiometrically monitored.

The disclosed analyte test strips may include a biochemical-responsive, including an analyte-responsive enzyme and an optional redox mediator. For example, a glucose oxidase (GOD) or glucose dehydrogenase (GDH) can be used when the analyte is glucose. A lactate oxidase can be used when the analyte is lactate. Hydroxybutyrate dehydrogenase can be used when the analyte is a ketone. In order to facilitate electrochemical reaction, the analyte test strip may further include an enzyme co-factor. For example, suitable cofactors include pyrroloquinoline quinone (PQQ), nicotinamide adenine dinucleotide $NAD^+$ and flavin adenine dinucleotide (FAD).

In some embodiments, enzymes catalyze the electrolysis of an analyte by transferring electrons between the analyte and an electrode, often the anode, through a redox mediator. In one embodiment, the analyte-responsive enzyme is disposed on the anode. In certain embodiments, the analyte-responsive enzyme is immobilized on the anode by, for example, cross linking the analyte-responsive enzyme with a redox mediator on the anode, thereby providing a sensing layer on the anode. In an alternative embodiment, the analyte-responsive enzyme is disposed adjacent to the anode. Generally, the analyte-responsive enzyme and redox mediator are positioned in close proximity to the anode in order to provide for electrochemical communication between the analyte-responsive enzyme and redox mediator and the anode. Generally, the analyte-responsive enzyme and redox mediator are positioned relative to the cathode such that electrochemical communication between the analyte-responsive enzyme and the redox mediator and the cathode is minimized.

Additional analyte-responsive enzymes and cofactors which may be suitable with the analyte test strips disclosed herein are described in U.S. Pat. No. 6,736,957, the disclosure of which is herein incorporated by reference. In certain embodiments, the redox species is a transition metal compound or complex. The transition metal compounds or complexes may be osmium, ruthenium, iron, and cobalt compounds or complexes. Suitable redox mediators and methods for producing them are described in U.S. Pat. Nos. 5,262,035; 5,264,104; 5,320,725; 5,356,786; 6,592,745; and 7,501,053, the disclosure of each of which is herein incorporated by reference.

Examples of suitable in vitro electrochemical analyte sensors and methods for making them which may be adapted to include a cathode and/or reference having a ceria nanoparticle composition as described herein include, but are not limited to, those described in U.S. Patent Application Publication Nos. 2007/0095661; 2006/0091006; 2006/0025662; 2008/0267823; 2007/0108048; 2008/0102441; 2008/0066305; 2007/0199818; 2008/0148873; 2007/0068807; 2009/0095625; and U.S. Pat. Nos. 6,616,819; 6,143,164; and 6,592,745; the disclosures of each of which are incorporated herein by reference in their entireties for all purposes.

In vitro analyte sensors may take a number of different forms depending on the particulars of a given sensor. For example, the sensors may be "tip fill" sensors, where the sample fluid is contacted at an aperture positioned at a proximal tip or leading edge or front of the sensor for introducing the sample fluid into the sample chamber of the sensor. Alternatively, the sensors may be "side fill" sensors, where the sample fluid is contacted at an aperture positioned at an edge other than a proximal tip, e.g., at a side edge of the sensor for introducing the sample fluid into the sample chamber of the sensor. Moreover, the sensors may have any desired electrode configuration. For example, the sensors may have the anode and cathode disposed on a single substrate in a coplanar configuration. Alternatively, the sensors may have the anode and cathode on separate substrates and in a facing configuration.

In certain embodiments, sensor test strips include a first substrate having a proximal end and a distal end, the first substrate defining a first side edge and a second side edge of the sensor extending from the proximal end to the distal end of the first substrate, the distal end being configured and arranged for insertion into an analyte measurement device, such as a glucose meter. According to this embodiment, the sensor test strips further include a second substrate disposed over the first substrate, a anode disposed on one of the first and second substrates, a cathode disposed on one of the first and second substrates, and a spacer disposed between the first and second substrates and defining a sample chamber that comprises the anode and the cathode.

The substrate may be any suitable non-conducting material, including, but not limited to polymeric, plastic, glass, silicon-containing material, dielectric material, or ceramic material, among other non-conducting materials. In some embodiments, the substrate is a flexible, deformable or thermoplastic substrate of polycarbonate, polyester (e.g., polyethylene terephthalate (PET)), polyvinyl chloride (PVC), polyurethane, polyether, polyamide, polyimide, combinations or copolymers thereof, such as glycol-modified polyethylene terephthalate. In other embodiments, the substrate may be a rigid substrate to, for example, provide structural support against bending or breaking Examples of rigid materials that may be used as the substrate include low conductivity ceramics, such as aluminum oxide and silicon dioxide. A substrate may also have a varying rigidity along a dimension of the substrate.

As indicated above, positioned between the first substrate and second substrate may be a spacer layer. In some embodiments, the spacer layer extends from the proximal end to the distal end of the sensor strip, or extends short of one or both ends. The spacer layer may be an inert non-conducting substrate, typically at least as flexible and deformable (or as rigid) as the first and second substrates. The thickness of the spacer layer may be constant throughout, and may range from 0.01 mm (10 µm) to 1 mm. For example, the thickness of the spacer may be between 0.02 mm (20 µm) and 0.2 mm (200 µm).

A sample chamber is defined by the space formed by the spacer layer between the first substrate and second substrate. For example, a portion of the spacer layer is removed to provide a volume between the first and second substrates. The volume of removed spacer is the sample chamber. Sample chambers may have a volume to receive a sample of biological fluid. In some embodiments, the sample chamber has a volume that is no greater than 1 µL, for example no greater than 0.5 µL, and also for example, no greater than 0.25 µL. A volume of no more than 0.1 µL is also suitable for sample chamber, as are volumes of no more than 0.05 µL and 0.03 µL.

The dimensions of sensor strips may vary. The overall length of sensor strips may range from 10 mm to 50 mm. For example, the length may be between 30 and 45 mm; e.g., between 30 to 40 mm. The overall width of sensor strips may range from 3 mm and no greater than 15 mm. For example, the width may be between 4 and 10 mm, e.g., between 5 to 8 mm, or between 5 to 6 mm. In one representative example, a sensor strip has a length of 32 mm and a width of 6 mm. In another representative example, a sensor strip has a length of 40 mm and a width of 5 mm. In yet another representative example, sensor strip 10 has a length of 34 mm and a width of 5 mm.

Methods for Determining Analyte Concentration

The ceria nanoparticle comprising cathodes and/or reference electrodes of electrochemical sensors (i.e., test strips) described herein find use in methods for determining the concentration of an analyte in a fluid sample from a subject. Generally, these methods include contacting a fluid sample with the sensor, generating a sensor signal at the working electrode, and determining the presence and/or concentration of the analyte using the sensor signal. It will be understood that the subject methods employ any of the cerium nanoparticle sensors described herein.

A variety of approaches may be employed to determine the concentration of the analyte. In certain aspects, an electrochemical analyte concentration determining approach is used. For example, determining the concentration of the analyte using the sensor signal may be performed by coulometric, amperometric, voltammetric, potentiometric, or any other convenient electrochemical detection technique.

After an analyte concentration is successfully determined, it may be displayed, stored, and/or otherwise processed to provide useful information. As demonstrated herein, the methods of the present disclosure are useful in connection with a device that is used to measure or monitor an analyte (e.g., glucose), such as any such device described herein. These methods may also be used in connection with a device that is used to measure or monitor another analyte, including oxygen, carbon dioxide, proteins, drugs, or another moiety of interest, for example, or any combination thereof, found in bodily fluid, including subcutaneous fluid, dermal fluid (e.g., sweat, tears, and the like), interstitial fluid, or other bodily fluid of interest, for example, or any combination thereof.

Examples of suitable methods for determining an analyte concentration using the electrochemical sensors having one or more cathodes or reference electrodes described herein include, but are not limited to, those described in U.S. Patent Application Publication Nos. 2007/0095661; 2006/0091006; 2006/0025662; 2008/0267823; 2007/0108048; 2008/0102441; 2008/0066305; 2007/0199818; 2008/0148873; 2007/0068807; U 2009/0095625; and U.S. Pat. Nos. 6,616,819; 6,143,164; and 6,592,745; the disclosures of each of which are incorporated herein by reference in their entireties.

Briefly, methods for using an in vitro sensor strip may include obtaining a biological fluid sample from a subject. The biological fluid sample may include, but is not limited to blood, plasma, interstitial fluid, dermal fluid, saliva, and tears. When the biological fluid is a blood sample, the sample may be obtained, e.g., using a lancet to create an opening in a skin surface. For example, the blood sample may be obtained from the finger of a subject. Alternatively, the blood sample may be obtained from a region of the subject having a lower nerve end density as compared to a finger. Obtaining a blood sample from a region having a lower nerve end density as compared to a finger is generally a less painful approach for obtaining a blood sample and may improve patient compliance, e.g., in the case of diabetes patient where regular monitoring of blood glucose levels is critical for disease management. The biological sample is then contacted the electrochemical sensor, generating a sensor signal at the anode, and determining the presence and/or concentration of the analyte using the sensor signal.

EXAMPLES

The following examples are offered by way of illustration and not by way of limitation. In this Experimental section, the term Ag/AgCl potential means the half-cell potential of the Ag/AgCl (3 M KCl) electrode at the temperature of the experiments, which was the ambient temperature of an air-conditioned laboratory, usually 23° C.±3° C. Also unless otherwise specified the experiments were carried out in the ambient laboratory atmosphere, i.e. under air.

For plasma treatment of the carbon a Harrick Plasma Cleaner purchased from Harrick Plasma Ithaca, N.Y. 14850 was used. For thermogravimetric analysis a Perkin-Elmer TGA-7 was used. Electrochemical cell, potentiostat and rotator: A 3-electrode electrochemical cell with a 3 mm diameter vitreous carbon working electrode; an Ag/AgCl reference electrode; and a platinum wire or carbon rod counter-electrode was used with a Model 832, CHI, Austin, Tex. potentiostat and a Pine Instrument rotator.

Unless otherwise stated, the voltammograms shown are first cycle voltammograms. Their scans start at the most oxidizing side (on the right).

Example 1

Ceria Nanoparticle Compositions for Reference Electrodes

Electrodes without Graphitic Carbon Particles:

1 mL of the ceria sol was diluted with 19 mL of de-ionized water. 2 mL of the resulting diluted sol was mixed with 0.2 mL of a 1 weight % aqueous solution of poly-N-vinylimidazole and with 2 µL of undiluted polyethylene glycol diglycidyl ether. 2 µL of the mixture was applied to the surface of the 3 mm diameter vitreous carbon electrode. The water was allowed to evaporate and the film was allowed to cure in ambient air and temperature overnight. The resulting films were readily water-wetted.

Electrodes with Graphitic Carbon Particles:

Plasma-treated C45 graphitic carbon from Timcal, Bodo, Switzerland was used in the coatings of the ceria nanoparticle reference electrodes. A mixture of 200 mg of freshly calcined ceria powder was mixed with 100 mg of plasma-treated hydrophilic graphitic C45 carbon and was dry-ground in an agate mortar. 2 mL water was added and the paste was ground for 10 min. 1.5 mL of the paste was mixed with 1.5 mL of an aqueous 1 weight % poly-N-vinylimidazole solution then mixture was sonicated for 20 min, then mixed with 3 mL of water containing 4 µL PEGDGE. Vitreous carbon electrodes of 3 mm diameter were coated by spreading a 2 µL droplet of the paste on their surface and the resulting film was cured overnight at room temperature. The resulting films were readily water-wetted.

When strong film-adhesion was sought a mixture of 200 mg of freshly calcined ceria powder was mixed with 100 mg of plasma-treated hydrophilic graphitic carbon and was dry-ground in an agate mortar. 2 mL water was added and the paste was ground for 10 min. 1.5 mL of the paste was mixed with 1.5 mL of an aqueous 1 weight % poly-N-vinylimidazole solution then mixture was sonicated for 20 min, then mixed with 3 mL of water containing 4 µL PEGDGE. 1 mL of the paste was mixed with 1 mL of 1 weight % PVI and 2 µL PEGDGE. A 2 µL droplet of the paste was applied and the resulting film was cured overnight at room temperature. The resulting films were readily water-wetted.

For the experiments in phosphate buffer, the paste was prepared by homogenizing a mixture of 1.0 mL of deionized water with 150 mg of the hydrophilic carbon, 1 mL of the oxygenated ceria sol by grinding in an agate mortar for about 20 min. 1.5 mL of the paste was then mixed with 1.5 mL of an aqueous 1 weight % poly-N-vinylimidazole solution and the mixture was sonicated for 20 min, then mixed with 3 mL of water containing 4 µL PEGDGE. The vitreous carbon electrodes of 3 mm diameter were coated by spreading a 2 µL droplet of the paste and dried overnight at room temperature. The resulting films were readily water-wetted.

Weak pH Dependence or pH-Independence of the Redox Potential in the pH 6-8 Range Relevant to Most Body Fluids.

Averaging the potentials of the anodic and cathodic wave-peaks of cyclic voltammograms measured at 1 mV/s scan rate showed that the redox potentials of the water-wetted as-purchased (oxygenated) ceria-carbon-polymer film-coated electrodes in 0.1 M NaCl-containing pH 6, pH 7 and pH 8, 20 mM phosphate buffers were respectively 0.14 V vs. Ag/AgCl at pH 6; 0.15 V at pH 7; and 0.15 V at pH 8.

Weak Dependence or Independence of the Redox Potential on $O_2$ Partial Pressure.

In pH 7, 20 mM imidazole-HCl buffer the redox potential of the water-wetted as-purchased (oxygenated) ceria-carbon-polymer film-coated electrodes, meaning here the point where the sum of the currents of the anodic and cathodic waves at 1 mV/s cyclic voltammograms was nil, was 0.13 V (Ag/AgCl under $N_2$; 0.13 V (Ag/AgCl) in air; and 0.13 V (Ag/AgCl) under $O_2$.

Effect of Heating of the Nanoparticles on the Redox Potential.

De-oxygenation of the ceria nanoparticles at 400° C. affected their 5 mV/s scan rate cyclic voltammograms. Under $O_2$, oxygen electroreduction was observed negative of −0.2 V (Ag/AgCl), the $O_2$ electroreduction current increasing up to −0.4 V (Ag/AgCl) then decreasing.

The redox potential of electrodes made with water wetted films containing de-oxygenated ceria nanoparticles, meaning nanoparticles that were heated to 400° C., also containing carbon and polymer, in 20 mM pH 7 imidazole buffer, was estimated by averaging the peak potentials of the electroreduction (cathodic) and the electrooxidation (anodic) waves. The redox potential was under $N_2$ 70 mV (Ag/AgCl). In pH 4 citrate buffer it was under $N_2$ 75 mV (Ag/AgCl); under air it was 0.10 V (Ag/AgCl); and under $O_2$ it was 0.175 V (Ag/AgCl).

Currents and Redox Potential of an Electrode with a Ceria Nanoparticle Coating without Carbon.

Comparison of the 1 mV/s cyclic voltammograms of electrodes with and without carbon-containing in their coatings showed that carbon increased the current about 100-fold but did not change greatly the redox potential, which was 0.05 V (AgCl).

Example 2

Rapid Wetting of Conductive Ceria Nanoparticle Compositions for Cathodes

Slowly Wetted Composition:

Electrodes were coated with a conductive composition containing Nafion, ceria nanoparticles and carbon at 1:1:1 weight ratio. 0.375 mg of solids in a paste of about 2.5 µL volume was loaded on 6 mm diameter carbon discs. The films were cured at 95-105° C. for 3 hours. The films were slowly wetted and water drops did not spread on them for more than 20 sec after the drop was applied.

Rapidly Wetted Composition 1:

Conductive ceria nanoparticle compositions were produced from C45 graphitic carbon and 10-20 nm particle size $CeO_{2-x}$ and an aqueous solution of trifluoroacetic acid (TFA). To 100 mg of graphite, 0.5 mL of an aqueous solution of TFA (0.1 w/v %) was added so that the carbon was well wetted by the solution. The wetting required 2 minutes. Next, 0.5 mL of the aqueous 0.1 w/v % TFA solution and 0.5 mL of colloidal $CeO_{2-x}$ (with acetate counter ion, $CeO_2$ (OAc)) were added and the mixture was ground for 20 minutes. An additional 0.5 mL of the aqueous 0.1 w/v % TFA solution was added and the mixture was ground for an additional 5 minutes.

Rapidly Wetted Composition 2:

Conductive ceria nanoparticle compositions were produced from C45 graphitic carbon and 10-20 nm particle size $CeO_{2-x}$ and aqueous HCl. To 100 mg of graphite, 0.5 mL of an aqueous solution of HCl (0.1 N) was added so that the carbon was well wetted by the solution. The wetting required 2 minutes. Next, 0.5 mL of the aqueous 0.1 N HCl solution and 0.5 mL of colloidal $CeO_{2-x}$ (with acetate counter ion, $CeO_2$ (OAc)) were added and the mixture was ground for 20 minutes. An additional 0.5 mL of the aqueous 0.1 N HCl solution was added and the mixture was ground for an additional 5 minutes.

Rapidly Wetted Composition 3:

Conductive ceria nanoparticle compositions were produced from C45 graphitic carbon and 10-20 nm particle size $CeO_{2-x}$ and an aqueous solution of perfluorooctanoic acid (PFOA). To 100 mg of graphite, 0.5 mL of an aqueous solution of PFOA (0.1 w/v %) was added so that the carbon was well wetted by the solution. The wetting required 2 minutes. Next, 0.5 mL of the aqueous 0.1 w/v % of PFOA solution and 0.5 mL of colloidal $CeO_{2-x}$ (with acetate counter ion, $CeO_2$ (OAc)) were added and the mixture was ground for 20 minutes. An additional 0.5 mL of the aqueous 0.1 w/v % PFOA solution was added and the mixture was ground for an additional 5 minutes.

Rapidly Wetted Composition 4:

Conductive ceria nanoparticle compositions were produced from C45 carbon and 10-20 nm particle size $CeO_{2-x}$ and an aqueous solution of acetic acid. To 100 mg of graphite, 0.5 mL of an aqueous solution of acetic acid (0.1 w/v %) was added so that the carbon was well wetted by the solution. The wetting required 2 minutes. Next, 0.5 mL of the aqueous 0.1 w/v % of acetic acid solution and 0.5 mL of colloidal $CeO_{2-x}$ (with acetate counter ion, $CeO_2(OAc)$) were added and the mixture was ground for 20 minutes. An additional 0.5 mL of the aqueous 0.1 w/v % acetic acid solution was added and the mixture was ground for an additional 5 minutes.

Example 3

Storage of Oxygen by Compositions for Cathodes

A conductive ceria nanoparticle composition as prepared in rapidly wetted composition 4 above was allowed to dry in an open dish at ambient temperature and atmosphere. The resulting powder was subjected to thermogravimetric analysis (TGA). The percentage of the weight lost was monitored while the powder was heated. Subsequently, $O_2$ gas was passed for 10 min through the composition before it was allowed to dry at ambient temperature and atmosphere. FIG. 1 illustrates that the powder from the oxygenated ceria nanoparticle composition above about 300° C. lost about 0.65% more of its weight than non-oxygenated ceria nanoparticle composition. Based on a molar mass of 172 g/mol for ceria and 32 g/mol for oxygen and since most the weight difference may be attributed to the binding of oxygen, 3.5 moles of oxygen per mole of ceria are bound in non-oxygenated ceria nanoparticles and 5.4 moles of oxygen per mole of ceria are bound in oxygenated ceria nanoparticles.

Example 4

Cathodes Having a Coating of a Conductive Ceria Nanoparticle Composition

Figure 2:
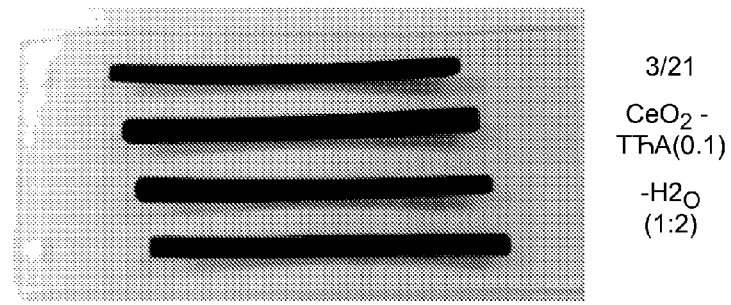
FIG. 2 shows example test-coupons for cathode materials made by coating plastic strips with conductive ceria nanoparticle compositions

Cathodes having a coating of the conductive ceria nanoparticle composition 1 described above were produced by drop-coating 30 µL of the conductive ceria composition on a 2.5 mm×34 mm (about 0.8 cm²) printable rough-side polyester strip. FIG. 2 shows examples of cathodes made by coating polyester substrates with a water wetted conductive ceria nanoparticle and carbon particle composition ("composition 1" above, having carbon and TFA).

Voltammetry and chronoamperometry studies showed that negative of threshold potentials, at pH 7, typically in the range −0.20V−−0.25 V (Ag/AgCl) reduction currents increased in an $O_2$ atmosphere.

Figure 3:
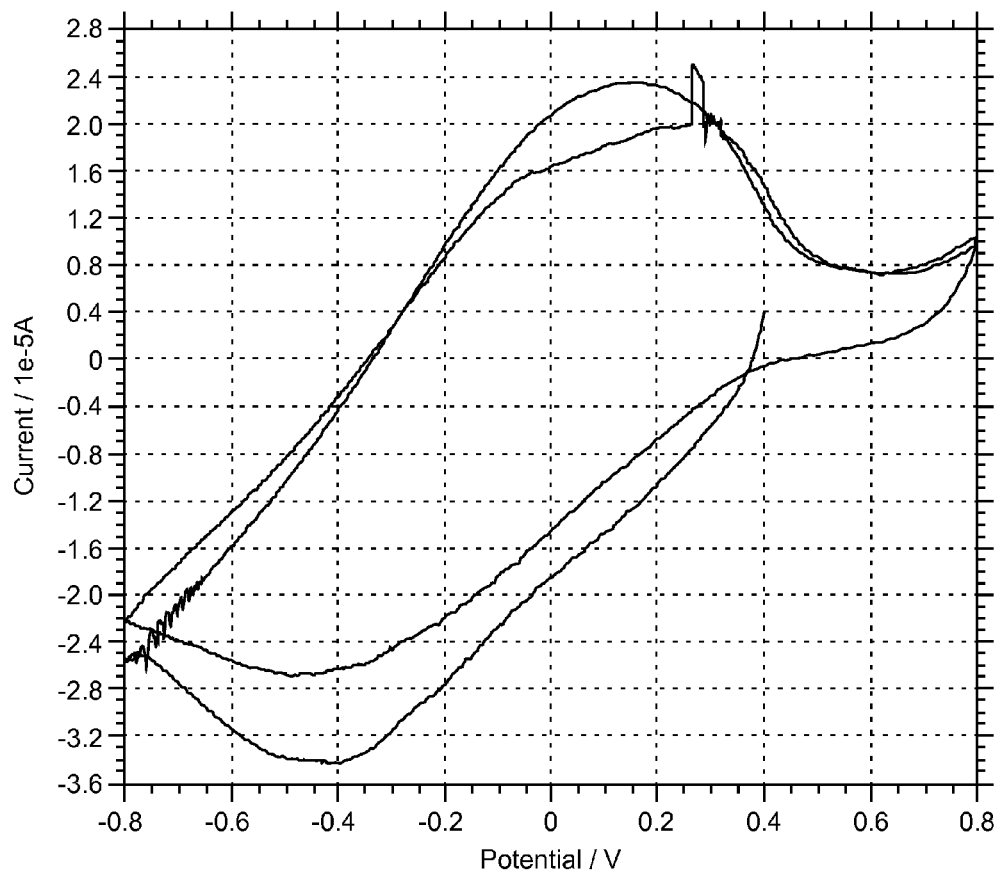
FIG. 3 shows an example cyclic voltammogram of an electrode employing a ceria nanoparticle composition.

An exemplary cyclic voltammogram of a 0.25 cm² electrode having a coating of the conductive ceria nanoparticle composition as described below is illustrated in FIG. 3. A 5 µL drop of the conductive ceria nanoparticle composition was applied to the surface of a Teijin-DuPont conductive polymer coated polyester sheet, aerated in 10 mM $KNO_3$. Cyclic voltammetry was performed with a platinum-wire counter-electrode and Ag/AgCl reference electrode with a scan rate of 1 mV/s.

Electrodes having a coating of the conductive ceria nanoparticle compositions were also tested by cyclic voltammetry using a 3-electrode cell, fresh pencil lead counter-electrode, Ag/AgCl reference electrode at pH 7.2, 0.1 M NaCl, 20 mM phosphate buffer solution. The conductive ceria nanoparticle composition was applied to the rough printable side of a polyester sheet. Both uncured and cured electrodes were measured by cyclic voltammetry. Uncured electrodes were dried at room temperature overnight. Cured electrodes were heat cured at 100° C. for the following periods: ceria nanoparticle-TFA, 5 hours; ceria nanoparticle-HCl, 3.5 hours, ceria nanoparticle-cetyl trimethylammonium bromide (CTAB), overnight.

Figure 4:
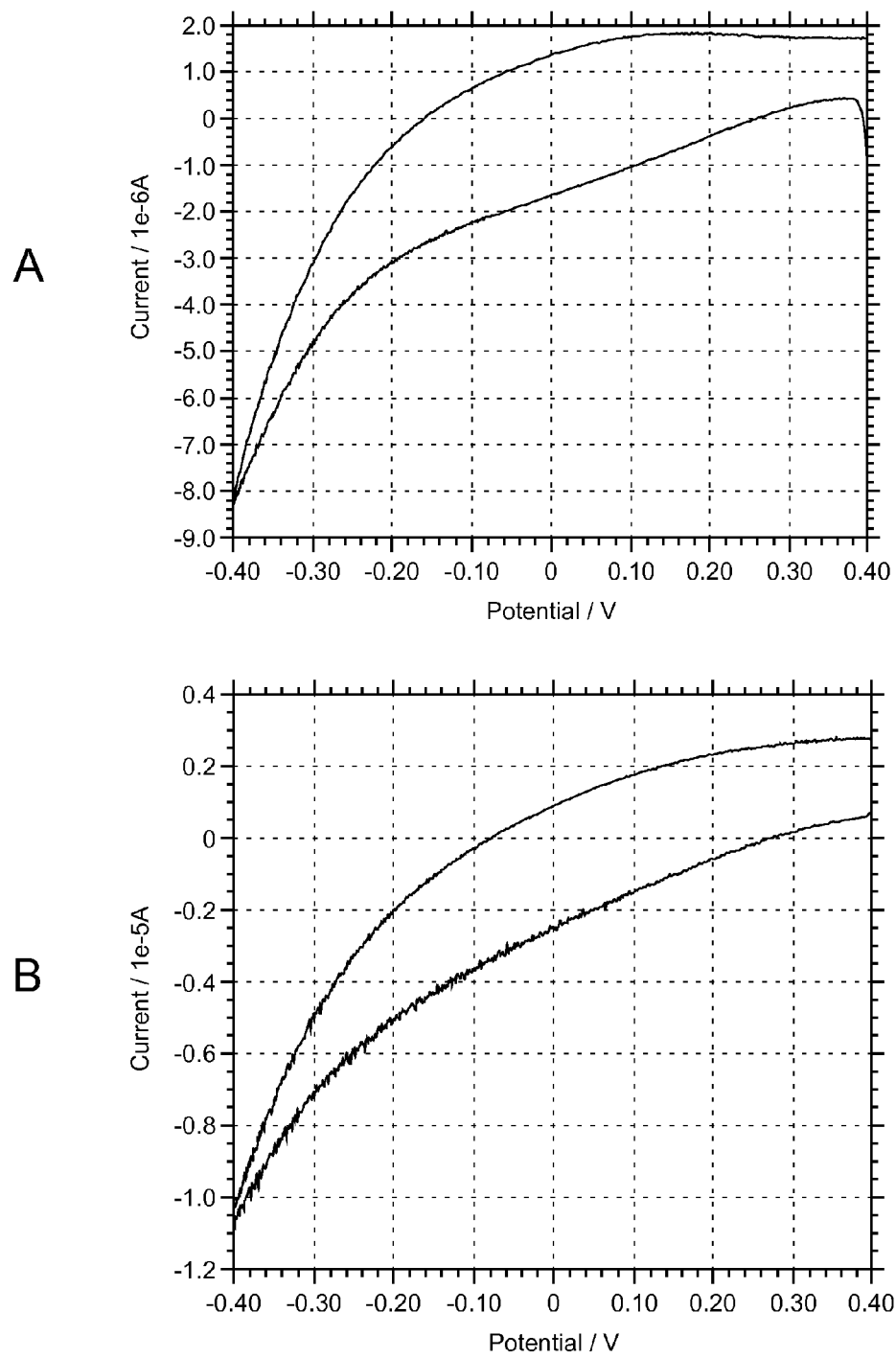
FIGS. 4A-B show cyclic voltammograms of electrodes with cured and uncured conductive coatings having ceria nanoparticles.
Figure 5:
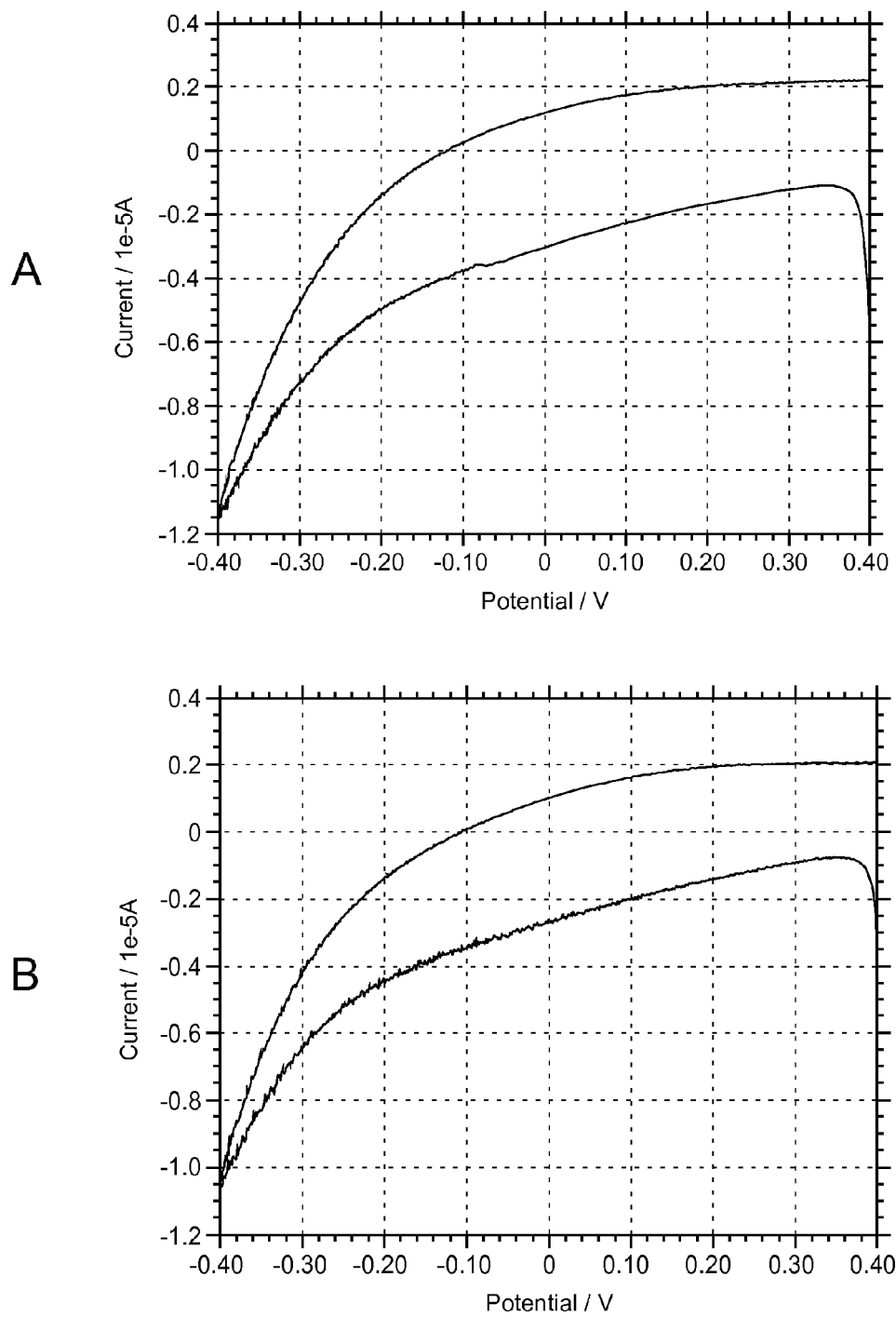
FIGS. 5A-B show cyclic voltammograms of electrodes with conductive coatings having ceria nanoparticles.
Figure 6:
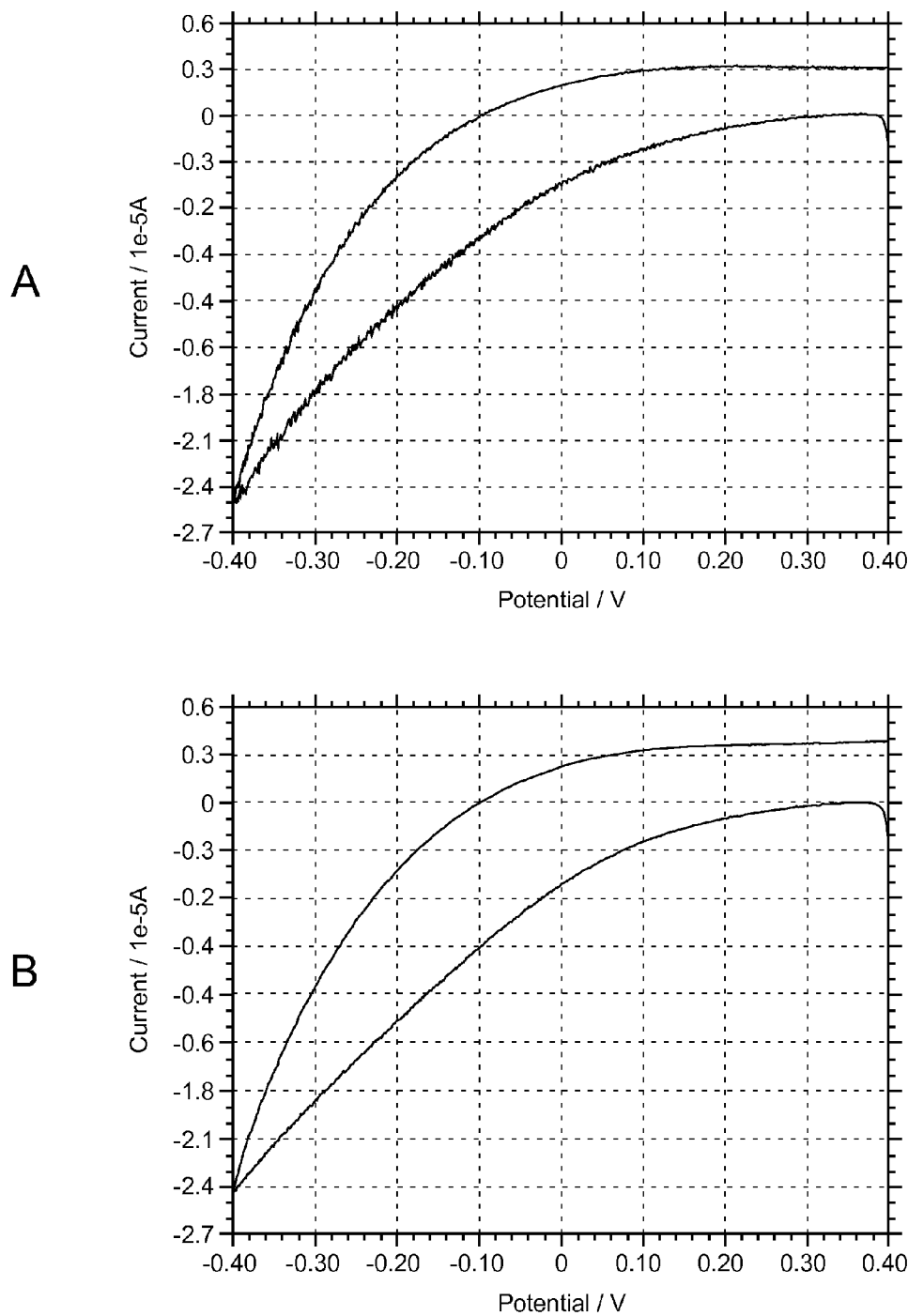
FIGS. 6A-D show cyclic voltammograms of electrodes with cured and uncured conductive coatings having ceria nanoparticle coatings and cetyl trimethylammonium bromide.
Figure 6:
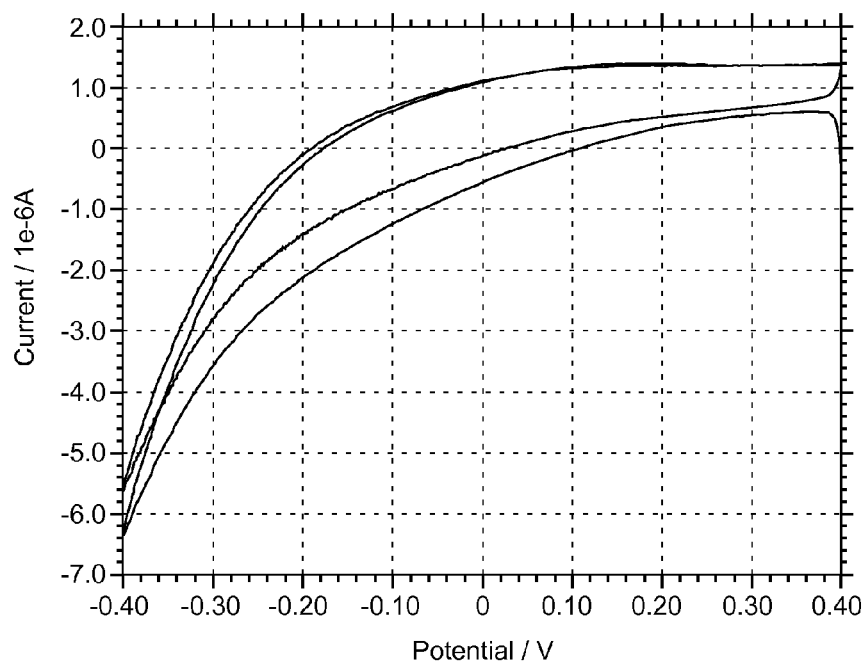
Figure 6:
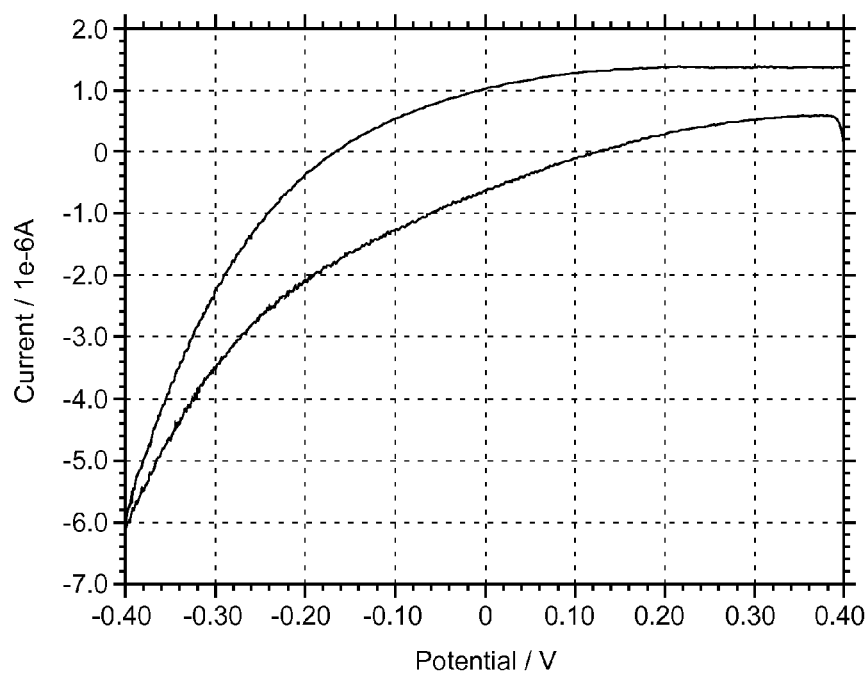

FIGS. 4-6 depict cyclic voltammograms for cured and uncured electrodes. FIGS. 4A and 4B depict cyclic voltammograms for uncured and cured electrodes, respectively, having a coating of the ceria nanoparticle-TFA composition (composition 1) diluted with water at a 1:1 ratio. FIGS. 5A and 5B depict cyclic voltammograms for uncured and uncured electrodes, respectively, having a coating of the ceria nanoparticle-HCl composition (composition 2) diluted with water at 1:2 ratio. FIGS. 6A and 6B depict cyclic voltammograms for cured and uncured electrodes, respectively, having a coating of the ceria nanoparticle-CTAB composition diluted with water at a 1:1 ratio. FIGS. 6C and 6D depict cyclic voltammograms for cured and uncured electrodes, respectively, having a coating of the ceria nanoparticles-CTAB composition diluted with water at 4:7 ratio.

Example 5

Redox Activity of Ceria and of Oxygenated Ceria and Operation in Serum

Poly-N-vinylimidazole was prepared by polymerizing N-vinylimidazole (see e.g., Ohara et al. *Anal. Chem.* 1993, 65, 3512-3517). Polyethyleneglycol diglycidyl ether (PEGDGE) was used as a crosslinking agent. Carbon powder was made hydrophilic by exposing it to a low-pressure air-plasma for 10 min. Acetic acid-stabilized 20 wt. %, pH 3 colloidal ceria nanoparticles (see e.g., composition Example above) was oxygenated by passing through it $O_2$ for 10 minutes.

A paste was prepared by homogenizing a mixture of 1.0 mL of deionized water with 150 mg of the hydrophilic carbon, 1 mL of the oxygenated ceria nanoparticles by grinding in an agate mortar for about 20 minutes. 1.5 mL of the paste was then mixed with 1.5 mL of an aqueous 1.0 wt. % poly-N-vinylimidazole solution and the mixture was ultrasonicated for 20 minutes, then mixed with 3.0 mL of water containing 4 μL PEGDGE.

Figure 7:
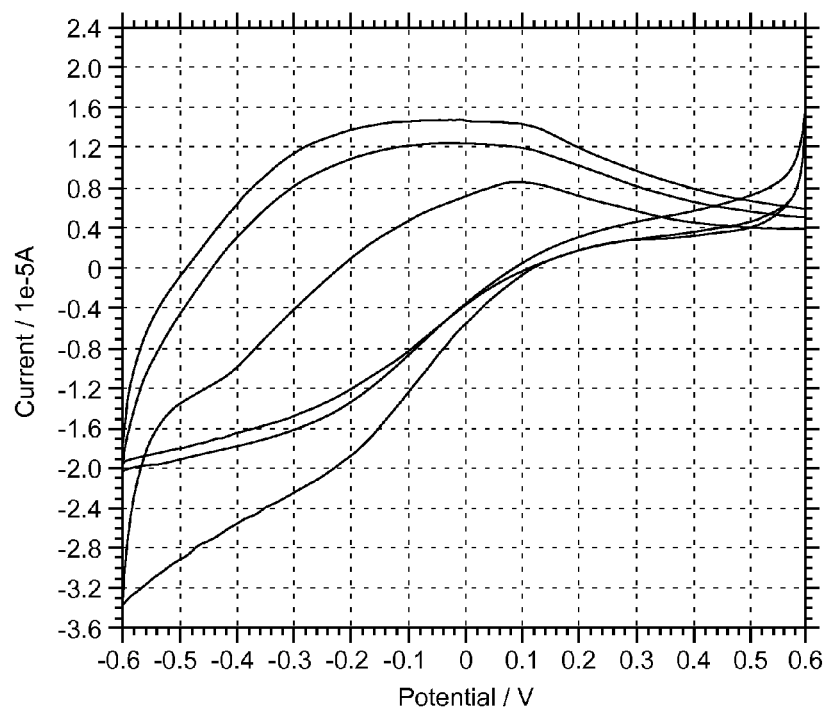
FIG. 7 shows a cyclic voltammogram of an electrode made by coating a plastic strip having a conductive polymer layer, the conductive polymer layer coated with a conductive composition having ceria nanoparticles.

Vitreous carbon electrodes of 5 mm diameter, each having a surface area of 0.78 cm$^2$, were coated by applying a 2 μL drop of the above paste to their surface. After drying, a second 2 μL drop was applied on top of the dried film. After drying at ambient temperature for 6 hours, the coating was cured at 70° C. for 10 minutes. FIG. 7 depicts voltammograms measured at 1 mV/s scan rate in a three-electrode cell, equipped with a platinum wire counter-electrode and an Ag/AgCl reference electrode. Current is reported in amperes. (i.e., 1×10$^{-5}$ A is equal to 10 microamperes). The upper voltammogram was observed when nitrogen was passed through the cell; the one below, when air was passed; and the lowest (highest current at −0.6 V) voltammogram was observed when oxygen was passed. There was little difference between the voltammograms in air and under nitrogen.

Figure 8:
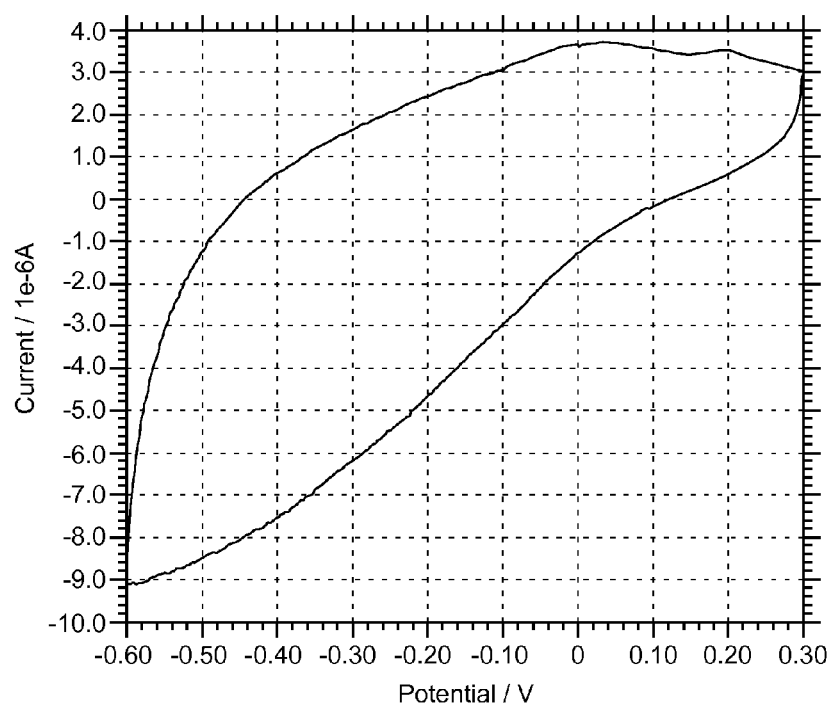
FIG. 8 shows a cyclic voltammogram of an electrode in calf serum, the electrode made by coating with a conductive composition having ceria nanoparticles, on a plastic strip coated with a conductive polymer film.

FIG. 8 shows a 1 mV/s scan rate cyclic voltammogram of the above electrode measured when the electrolyte in the cell was newborn calf serum and the atmosphere was air.

Figure 9:
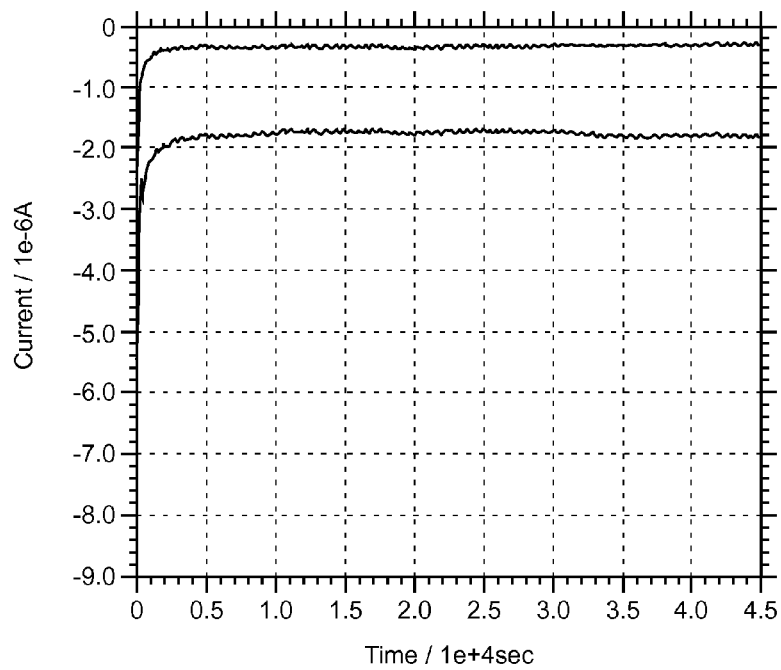
FIG. 9 shows the persistence of the electroreduction current of a vitreous carbon electrode coated with a composition having ceria nanoparticles, carbon particles and a hydrophilic polymer.

FIG. 9 shows the persistence of the electroreduction current of a 3 mm diameter vitreous carbon electrode coated with a mixture having conductive carbon, ceria nanoparticles, and poly-N-vinylimidazole cross-linked with polyethylene glycol diglycidyl ether in a solution under air. The electrolyte contained 20 mM imidazole and its pH was 7. The upper curve (i.e., curve located at about 0.5 microamperes) is for an electrode poised at the potential of the Ag/AgCl electrode (3 M KCl). The lower curve (i.e., curve located at about 2 microamperes) is for the same electrode poised at −0.2 V versus the potential of the Ag/AgCl electrode (3 M KCl).

Example 6

Electrode without Added Conductor

Figure 10:
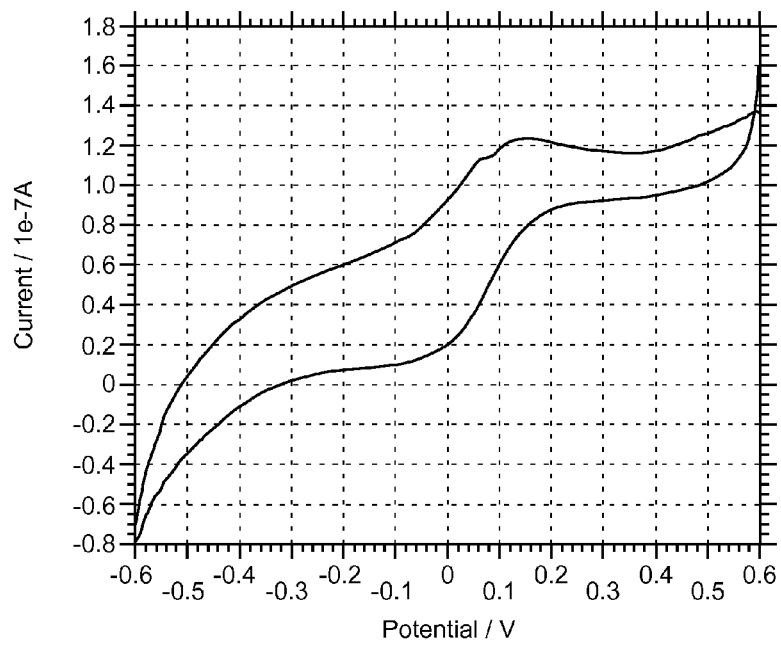
FIG. 10 shows a cyclic voltammogram of a vitreous carbon electrode at 1 mV/s scan rate, in a nitrogen atmosphere.

FIG. 10 shows a cyclic voltammogram of a 3 mm diameter vitreous carbon electrode at 1 mV/s scan rate, in a nitrogen atmosphere. The electrode was coated with a film containing only ceria nanoparticles and polyethylene glycol diglycidyl ether-crosslinked poly-N-vinylimidazole. The electrolyte is pH 7, 20 mM imidazole-HCl buffer. Anodic (electrooxidation) and cathodic (electroreduction) waves are observed. The redox potential is about 70 mV versus Ag/AgCl in 3 M KCl. The 1 e-7 A units of the current shown are 10$^{-7}$ A.

Example 7

Redox Activity of Strip Coatings with a Ceria Nanoparticle Composition with Graphite The exemplary 1 mV/s scan rate cyclic voltammograms of FIGS. 11-15 show initial scans, suggesting currents and coulombic capacities; the scans started at the most positive potentials.

Example 8

Figure 11:
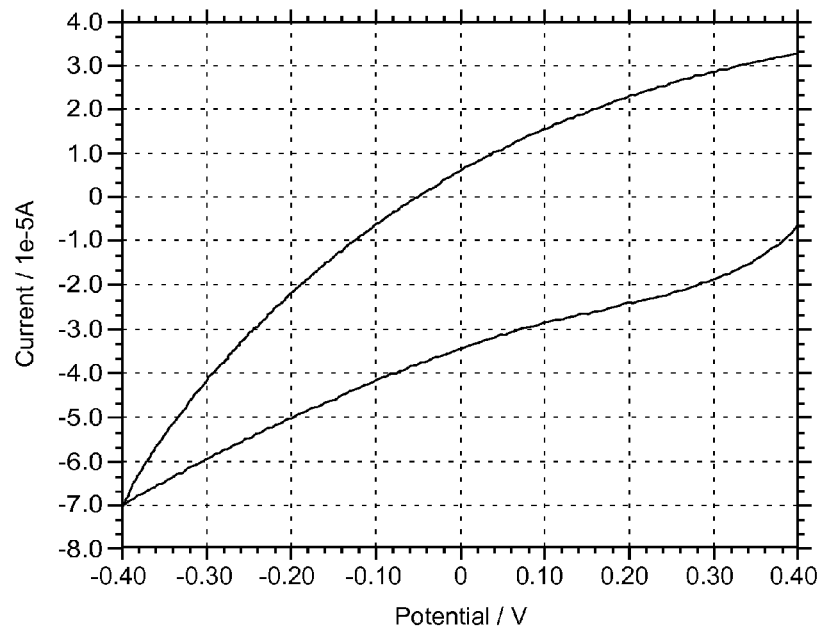
FIG. 11 shows the first cycle, 100 mV/s scan rate voltammogram of an electrode made by coating a plastic strip with a composition having carbon, ceria nanoparticles and cetyltrimethylammonium bromide (CTAB).

A conductive ceria nanoparticles composition was prepared by grinding in an agate mortar a mixture of 30.6 mg of carbon with 0.50 ml of 20 wt. %, pH 3, acetic acid stabilized ceria nanoparticles and with 1.5 mL of aqueous 0.10 w/v % cetyl trimethylammonium bromide (CTAB) solution. 2 mL of deionized water was added and the mixture was re-homogenized by grinding. The composition was applied to the inkjet printable side of a polyester OHP (overhead projector) transparency film substrate. The film was cut to strips of 2 mm×30 mm, each strip having an area of 0.6 cm$^2$. The composition was coated on the printable side of the strip by spreading on it a 30 μL drop of the composition. The coating was allowed to dry overnight at room temperature, where the first-cycle voltammogram of the resulting electrode was measured in a three-electrode cell, equipped with a carbon rod counter-electrode and an Ag/AgCl reference electrode. The electrolyte in the cell was aqueous 100 mM NaCl, 20 mM phosphate at pH 7. For the measurement, 13 mm of the 2 mm wide strip, having an area of 0.26 cm$^2$, was immersed in the electrolyte. FIG. 11 shows the first cycle, 100 mV/s scan rate voltammogram of the 0.26 cm$^2$ electrode made by coating a plastic strip with a composition having carbon, ceria nanoparticles and cetyltrimethylammonium bromide (CTAB).

Example 9

Figure 12:
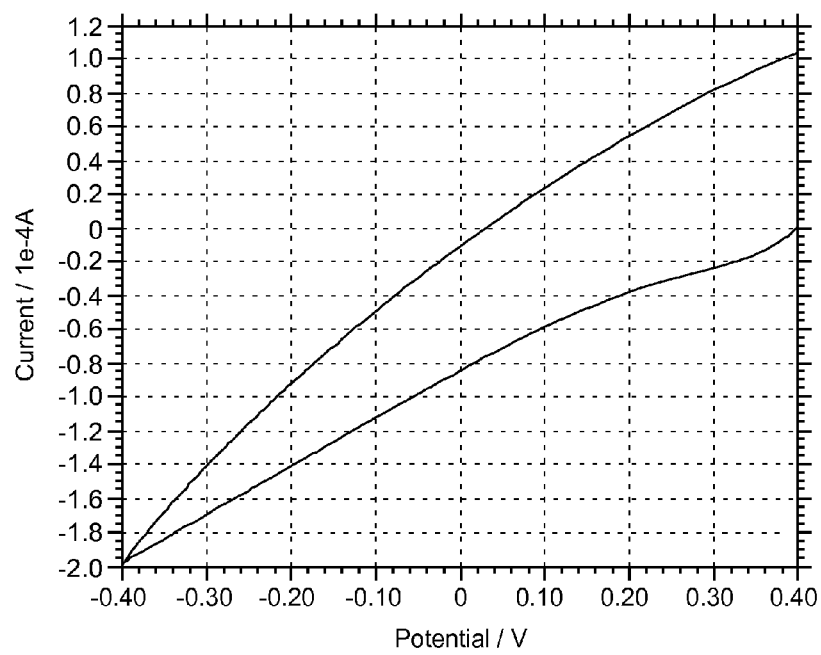
FIG. 12 shows the first cycle, 100 mV/s scan rate voltammogram of an electrode made by coating a plastic strip with a composition having carbon, ceria nanoparticles and 1,2-diaminopropane.

A conductive ceria nanoparticles composition was prepared by grinding in an agate mortar a mixture of 30.6 mg of carbon with 0.50 ml of 20 wt. %, pH 3, acetic acid stabilized ceria nanoparticles and with 1.5 mL of aqueous 0.10 w/v % 1,2-diaminopropane solution. 1 mL of deionized water was added and the mixture was re-homogenized by grinding. The composition was applied to the inkjet printable side of an overhead projector transparency film polyester substrate. The film was cut to strips of 2 mm×30 mm, each strip having an area of 0.6 cm$^2$. The composition was coated on the strip by spreading on it a 30 μL drop of the composition. The coating was allowed to dry overnight at room temperature, where the first-cycle voltammogram of the resulting electrode was measured in a three-electrode cell, equipped with a carbon rod counter-electrode and an Ag/AgCl reference electrode. The electrolyte in the cell was aqueous 100 mM NaCl, 20 mM phosphate at pH 7. For the measurement, 13 mm of the 2 mm wide strip, having an area of 0.26 cm$^2$, was immersed in the electrolyte. FIG. 12 shows the first cycle, 100 mV/s scan rate, voltammogram of the 0.26 cm$^2$ electrode made by coating a plastic strip with a composition having carbon, ceria nanoparticles and 1,2-diaminopropane.

Example 10

Figure 13:
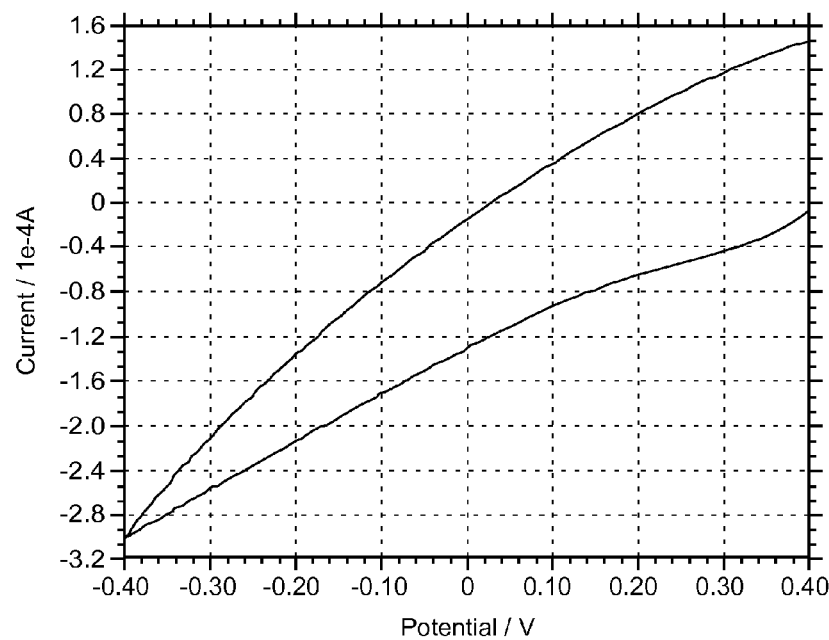
FIG. 13 shows the first cycle, 100 mV/s scan rate voltammogram of an electrode made by coating a plastic strip with a mixture having carbon, ceria nanoparticles, 1,2-diaminopropane and polymethacryloxyethyltrimethylammonium bromide.

A conductive ceria nanoparticles composition was prepared by grinding in an agate mortar a mixture of 100 mg of carbon with 0.50 ml of 20 wt. %, pH 3, acetic acid stabilized colloidal ceria nanoparticles and with 1.5 mL of aqueous 0.10 w/v % 1,2-diaminopropane solution. 2 mL of deionized water and 2 mL of a 1.0 wt. % solution of polymethacryloxyethyltrimethylammonium bromide in water were added and the mixture was re-homogenized by grinding. The composition was applied to the inkjet printable side of a polyester OHP (overhead projector) transparency film substrate. The film was cut to strips of 2 mm×30 mm, each strip having an area of 0.6 $cm^2$. The composition was coated on the printable side of the strip by spreading on it a 30 µL drop of the composition. The coating was allowed to dry overnight at room temperature, where the first-cycle voltammogram of the resulting electrode was measured in a three-electrode cell, equipped with a carbon rod counter-electrode and an Ag/AgCl reference electrode. The electrolyte in the cell was aqueous 100 mM NaCl, 20 mM phosphate at pH 7. For the measurement, 13 mm of the 2 mm wide strip, having an area of 0.26 $cm^2$, was immersed in the electrolyte. FIG. 13 shows the first cycle, 100 mV/s scan rate voltammogram of the 0.26 $cm^2$ electrode made by coating a plastic strip with a mixture having carbon, ceria nanoparticles, 1,2-diaminopropane and polymethacryloxyethyltrimethylammonium bromide.

Example 11

Figure 14:
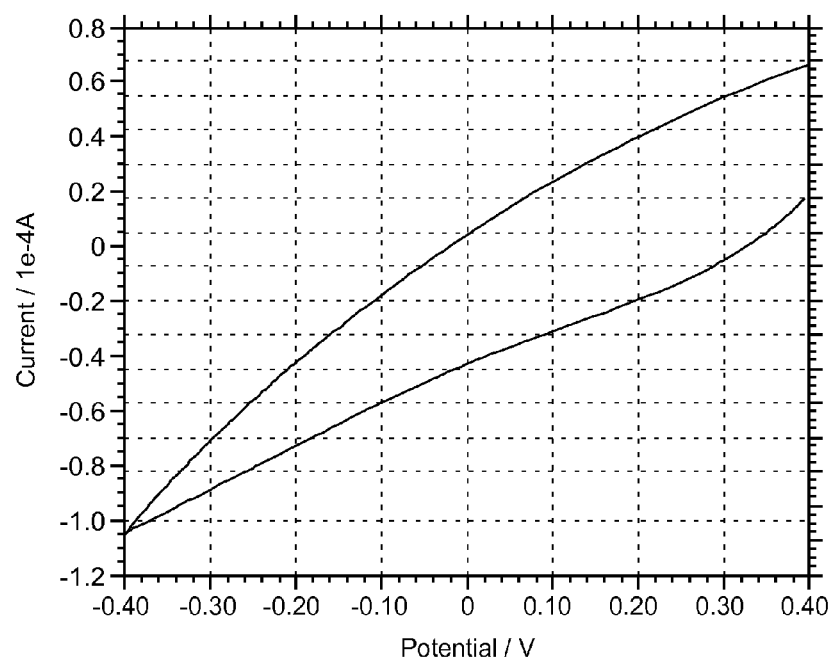
FIG. 14 shows the first cycle, 100 mV/s scan rate voltammogram of an electrode made by coating a plastic strip with a composition having carbon, ceria nanoparticles and polyethyleneimine.

A conductive ceria nanoparticles composition was by grinding in an agate mortar a mixture of 150 mg of carbon with 0.50 mL of 20 wt. %, pH 3, acetic acid stabilized colloidal ceria nanoparticles and with 2.0 mL of 0.10 N hydrochloric acid. 5 mL of deionized water and 2.5 mL of 1.0 wt. % solution of polyethyleneimine ($M_n$ 60,000; $M_w$ 750,000) in water were added and the mixture was re-homogenized by grinding. The composition was applied to the inkjet printable side of a polyester OHP (overhead projector) transparency film substrate. The film was cut to strips of 2 mm×30 mm, each strip having an area of 0.6 $cm^2$. The composition was coated on the printable side of the strip by spreading on it a 30 µL drop of the composition. The coating was allowed to dry overnight at room temperature, where the first-cycle voltammogram of the resulting electrode was measured in a three-electrode cell, equipped with a carbon rod counter-electrode and an Ag/AgCl reference electrode. The electrolyte in the cell was aqueous 100 mM NaCl, 20 mM phosphate at pH 7. For the measurement, 13 mm of the 2 mm wide strip, having an area of 0.26 $cm^2$, was immersed in the electrolyte. FIG. 14 shows the first cycle, 100 mV/s scan rate voltammogram of the 0.26 $cm^2$ electrode made by coating a plastic strip with a composition having carbon, ceria nanoparticles and polyethyleneimine.

Example 12

Figure 15:
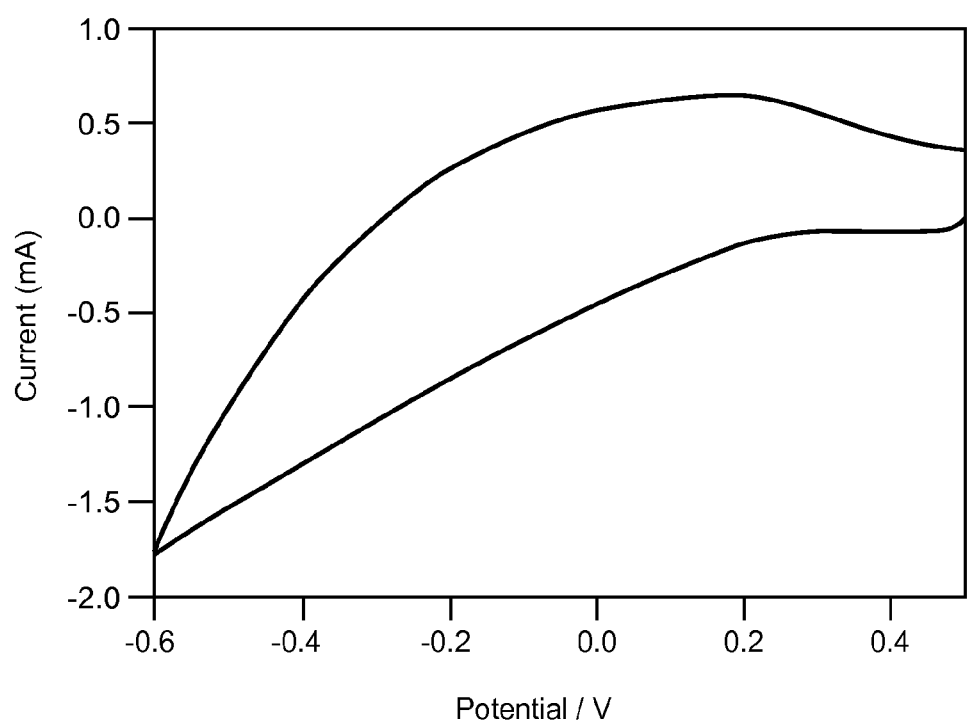
FIG. 15 shows the first cycle, 100 mV/s scan rate voltammogram of an electrode made by coating a screen printed carbon electrode with a composition having carbon, ceria nanoparticles, poly-N-vinylimidazole and polyethylene glycol diglycidyl ether.

Poly-N-vinylimidazole was prepared by polymerizing N-vinylimidazole (see e.g., Ohara et al. *Anal. Chem.* 1993, 65, 3512-3517). Polyethyleneglycol diglycidyl ether (PEGDGE) was used as a crosslinking agent. Carbon powder was made hydrophilic by exposing it to a low-pressure air-plasma for 10 min. Acetic acid-stabilized 20 wt. %, pH 3 colloidal ceria nanoparticles was oxygenated by passing through it $O_2$ for 10 minutes. 5 mm diameter, screen printed, graphitic carbon electrodes were exposed, prior to their coating, to a low-pressure air-plasma for 3 min. A conductive ceria nanoparticles composition was prepared by homogenizing a mixture of 1.0 mL of deionized water with 150 mg of the hydrophilic carbon, 1 mL of the oxygenated ceria nanoparticles by grinding in an agate mortar for about 20 minutes. 1.5 mL of the composition was then mixed with 1.5 mL of an aqueous 1.0 wt. % poly-N-vinylimidazole solution and the mixture was ultrasonicated for 20 minutes, then mixed with 3.0 mL of water containing 4 µL PEGDGE. The carbon electrodes were coated by applying and spreading a 2 µL drop of the composition to the surface, followed by drying the resultant film. A second 2 µL drop was applied and spread. After drying at ambient temperature for 6 hours, the coating was cured at 70° C. for 10 min. FIG. 15 shows the first-cycle 100 mV/s scan-rate voltammogram of the 0.79 $cm^2$ electrode made by coating a screen printed carbon electrode with a composition having carbon, ceria nanoparticles, poly-N-vinylimidazole and polyethylene glycol diglycidyl ether. The electrolyte in the cell was aqueous 100 mM NaCl, 20 mM phosphate at pH 7. The voltammogram was obtained in a three-electrode cell, equipped with a platinum wire counter-electrode and an Ag/AgCl reference electrode.

Example 13

A paste was prepared by spreading a 1.0 mL of 0.1 weight/volume % solution of 1,2-diaminopropane (DAP) in water with 150 mg of Timcal Super-P—Li carbon allowing the carbon to wet for 5 min. 1.0 mL of the 20 weight % ceria nanoparticle (acetic acid type) sol from Nyacol was added, followed by 0.5 mL of 0.1 weight/volume % solution of 1,2-diaminopropane (DAP) in water. The mixture was hand-ground to homogeneity in an agate mortar. 1 mL of the homogeneous paste was mixed with 1.0 mL 0.1 M aqueous HCl then with 1.0 mL of a 1 weight % aqueous solution of poly(methacryloxyethyl trimethylammonium bromide) (PMANBr). The mixture was shaken till homogeneous. 30 µL of the mixture was applied to form an about uniform coating on a 2 mm×30 mm polyester test coupon and allowed to dry overnight. A 13 mm long portion of the resulting electrode, with an area of 0.26 $cm^2$, contained was then immersed in a pH 7.2 aqueous 0.1 M NaCl, 20 mM phosphate buffered solution in the 3-electrode cell and was used as the working electrode. The potential was scanned at 100 mV/s, starting at +0.4 V and the current was measured. At −0.2 V (Ag/AgCl) applied potential the cathodic (i.e. electroreduction) current was 0.37±0.02 mA. The corresponding current density was about 1.5 mA $cm^{-2}$. Next, a fresh electrode was poised at −0.2 V (Ag/AgCl) and the dependence of the cathodic current on time was measured to determine the coulombic capacity. By integrating to 5 sec, a coulombic capacity of 2.1±0.1 mC was measured. The corresponding 5 sec coulombic capacity per $cm^2$ was 8 mC $cm^2$. By integrating to 20 sec, a coulombic capacity of about 6 mC was measured. The corresponding 20 sec coulombic capacity per $cm^2$ was 23 mC $cm^{-2}$.

Example 14

Ceria-Carbon-Poly-4-Vinylpyridine (P4VP) and Ceria-Carbon Polyvinylidene Fluoride (PVDF) Electrodes Preparation of Electrode Pastes.

An electrode paste was made that included, on a dry weight basis, 26% $CeO_2$, 26% carbon black, 6% graphite, 37% poly-4-vinylpyridine (ca. 20,000 MW) and 6% polyethylene glycol (MW 400) diglycidyl ether. The ceria-carbon mixture (referred to herein as "CeO2-C 0321B"), was prepared by combining 1.8 g carbon black, 0.4 g graphite, 7.4 mL ceria acetate colloid and 17.6 mL of 3% (v/v) acetic acid. The mixture had 4.0 g total solids (excluding acetate) in 25 mL total liquids or 16% solids. The material was mixed in a Fritsch Pulverisette 6 ball mill. It was found that this method is more reproducible than hand mixing in a mortar and pestle. The material was placed upon 100 g of 3 mm zirconia balls in an 80 mL zirconia grinding bowl. The mill was run at 400 rpm ("medium mixing") for 60 minutes, total. (The 60 minutes of mixing were divided into six 10 minute runs with 3 minutes "rest" and reversal in between.) The ceria-carbon mixture was withdrawn by pipette from among the milling balls.

The P4VP-based electrode paste was prepared by combining 1.0 mL of CeO2-C 0321B, 5.2 mL of 2% (w/v) poly-4-vinylpyridiene (in 1.2% (v/v) acetic acid) and 0.16 mL of 1:10 diluted PEGDGE. The paste has 0.14 g total solids (excluding acetate) in 3.2 mL total liquids, or 4.4% solids. First, 1 mL of CeO2-C, 5.2 mL of P4VP binder and 30 g of zirconia balls were milled for 20 minutes (twice 10 run+3 rest) at 400 rpm in the Pulverisette. It was found that this method produced a more homogeneous dispersion than vortex mixing, which can leave clumps which can cause cracking Second, 2.5 mL of the homogenized CeO2-C+P4VP was combined with 0.080 mL of 1:10 diluted PEGDGE and vortexed for 20 seconds.

Immediately after vortexing, the paste was pipetted and spread on a printed carbon electrode. The aliquot was almost always 5 µL in a 6 mm by 3 mm area, or 28 µL/cm$^2$. The printed carbon electrode was a commercially available screen-printed carbon electrode, typically, the carbon half of a blood glucose test strip. The electrode was prepared by exposing it to air plasma, due to an imperfect vacuum, for approximately one minute in a Harrick plasma cleaner operating at its medium rf power setting. Plasma treatment made it easily wetted. Its unused area was masked with a thin coat of nail polish to leave an approximately 6 mm by 3 mm test area at the end.

For single-layer tests, the paste was dried-cured on the electrodes overnight at room temperature (about 25° C.), sometimes in a 75-80% humidity chamber and sometimes in ambient humidity, which varied from about 20% to 50%. For multi-layer tests, the paste was dried under an infrared lamp. The 250 watt lamp was about 9 inches above the electrodes, the illuminated area temperature was 40° C. to 47° C., and the humidity was ambient. Lower temperatures (40-45° C.) gave nicer looking coatings than higher temperatures (45-47° C.). Drying times were about 20 minutes for the first layers and decreased to about 10 minutes for the last layers. Drying was assessed visually.

Electrode with Polyvinylidene Fluoride Binder.

Electrode pastes with PVDF were prepared the same way P4VP-based pastes were prepared, except that 0.5%, 1% or 2% (w/v) polyvinylidene fluoride (in N-methylpyrrolidone (NMP)) was substituted for the P4VP solution.

Coulombic Capacity.

The electrodes were tested for coulombic capacities by the amperometric i-t procedure. In a three electrode cell, the working electrode was the electrode described above, the reference was a Ag/AgCl (3 M KCl) electrode and the counter electrode was a platinum coil or a graphite rod. The solution in the cell was pH 7.2 buffer made with 20 mM phosphate and 100 mM sodium chloride. The potentiostat was a CH Instruments Model 660A, and its control and data acquisition were by CH Instruments software. Tests were run at room temperature, approximately 23° C. Before a test, the electrode was immersed in buffer for 1 minute. During a test, the electrode was poised at −0.2 V vs. the reference, and the current (i) as a function of time (t) was measured. The i-t data was integrated to give total charge passed as a function of time. The total charge passed after 6, 20, 250 and 1000 s was the coulombic capacity at those times.

Table 1 shows the coulombic capacities of electrodes made from different batches of P4VP-based electrode paste. For one-layer electrodes, the mean coulombic capacities were −0.96 and −1.6 mC/cm$^2$ in 6 and 20 seconds, respectively. For many one-layer electrodes, the current was approaching zero, and sometimes going slightly positive, before 250 seconds had elapsed. For five-layer electrodes, the mean coulombic capacities were −4.8, −13, −49 and −69 mC/cm$^2$ in 6, 20, 250 and 1000 seconds, respectively.

TABLE 1

Coulombic capacity test strips made from different batches of P4VP-based electrode paste.

| Note | Batch | Batch Prep'd | Homogenized | Strips Prep'd | n | mcoul/cm$^2$ at 6 sec mean | stdev | n | mcoul/cm$^2$ at 20 sec mean | stdev | n | mcoul/cm$^2$ 250 sec mean | stdev | n | mcoul/cm$^2$ at 1000 sec mean | stdev |
|---|---|---|---|---|---|---|---|---|---|---|---|---|---|---|---|---|
| | | | | | | 1 layer | | | | | | | | | | |
| 1 | 2 | 4/26 | 5/24 | 5/24 | 6 | −1.19 | 0.18 | 6 | −2.03 | 0.40 | | | | | | |
| 0 | 3 | 5/22 | 5/24 | 5/24 | 7 | −0.81 | 0.22 | 7 | −1.32 | 0.46 | | | | | | |
| 0 | 4 | 5/27 | 5/27 | 5/27 | 5 | −0.83 | 0.23 | 5 | −1.37 | 0.39 | | | | | | |
| 0 | 5 | 5/30 | 5/30 | 5/30 | 5 | −1.01 | 0.18 | 4 | −1.70 | 0.27 | | | | | | |
| | Mean | | | | | −0.96 | | | −1.62 | | | | | | | |
| | Range % | of mean | | | | 40% | | | 47% | | | | | | | |
| | | | | | | 5 layers | | | | | | | | | | |
| 1 | 1 | 3/21 | n/a | 4/9 | 4 | −4.63 | 0.54 | 4 | −12.42 | 1.61 | 4 | −47.92 | 9.49 | 4 | −67.62 | 14.44 |
| 1 | 2 | 4/26 | 5/24 | 5/24 | 3 | −4.78 | 0.46 | 3 | −12.93 | 1.18 | 3 | −52.52 | 6.86 | 3 | −75.44 | 11.20 |
| 0 | 3 | 5/22 | 5/24 | 5/24 | 3 | −4.28 | 0.50 | 3 | −11.21 | 1.30 | 3 | −39.66 | 5.34 | 3 | −54.54 | 8.05 |
| 0 | 4 | 5/27 | 5/27 | 5/29 | 3 | −4.18 | 0.20 | 3 | −11.25 | 0.67 | 3 | −40.71 | 6.96 | 3 | −56.54 | 11.05 |
| 0 | 5 | 5/30 | 5/30 | 5/30 | 3 | −6.32 | 0.48 | 3 | −17.24 | 1.34 | 3 | −65.00 | 7.77 | 3 | −91.49 | 11.98 |
| | Mean | | | | | −4.84 | | | −13.01 | | | −49.16 | | | −69.13 | |
| | Range % | of mean | | | | 44% | | | 46% | | | 52% | | | 53% | |
| | | | | | | 5 layers | | | | | | | | | | |
| 2 | 2 | 4/26 | 5/24 | 5/29 | 3 | −5.25 | 0.50 | 3 | −12.04 | 1.47 | 3 | −27.78 | 4.506 | 3 | −35.80 | 4.94 |
| 2 | 3 | 5/22 | 5/24 | 5/29 | 3 | −4.15 | 0.62 | 3 | −8.78 | 1.56 | 3 | −19.05 | 3.99 | 3 | −26.80 | 6.26 |
| 2 | 4 | 5/27 | 5/27 | 5/29 | 3 | −4.28 | 0.46 | 3 | −9.84 | 1.13 | 3 | −24.17 | 2.84 | 3 | −32.15 | 4.73 |

The theoretical capacity of a one-layer electrode was 32 milli-coulombs, based on the calculation below. Scaled by area, it was 180 mC/cm$^2$. The theoretical capacity of a five-layer electrode was 890 mC/cm$^2$. For one-layer electrodes, the mean coulombic capacity in 20 seconds was about 1% of the theoretical capacity. For five-layer electrodes, the mean coulombic capacity in 20 and 1000 seconds was about 1.5% and 8% of theoretical capacity. In 48 hour tests of two 20-layer electrodes, the coulombic capacity was 720 mC/cm$^2$, which was 20% of the theoretical capacity ([(5×10$^{-3}$ mL paste)×(4.4% solids in paste)×(26% CeO2 in solids)/(172 g/mol CeO$_2$)]×(96500 C/mol)).

For one group (ID: JW0724) of one-layer electrodes of PVDF-based electrode paste, the mean coulombic capacities were −1.8, −4.1 and −14 mC/cm$^2$ in 6, 20 and 250 seconds, respectively. For one group (ID: SC0729A) of six-layer electrodes, the mean coulombic capacities were −7.1, −19 and −74 mC/cm$^2$ in 6, 20 and 250 seconds, respectively.

Batch Reproducibility and Shelf Life.

For Batches #1 through #5, the relative standard deviation of the coulombic capacities was about 50%. Batch #5 raised the variability substantially, but there was no reason to exclude it from the dataset. Ceria-carbon pastes that were stored for 20 and 29 days before testing (Batches #1 and #2, respectively) had capacities that were comparable to the capacities of fresh pastes. Homogenized paste+binder mixtures that were stored for 2 and 5 days had long-run (250 and 1000 sec.) capacities that were about 50% lower than the capacities of fresh mixtures.

Cracking and Peeling.

Figure 16:
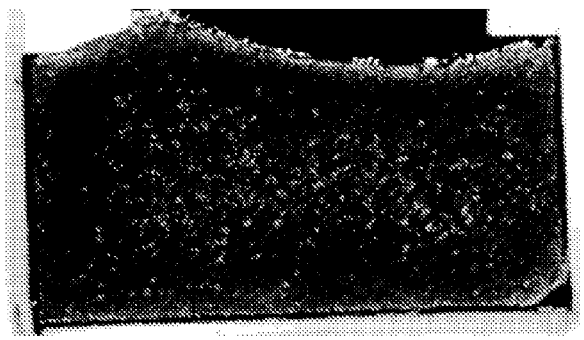
FIGS. 16A-D show a series of micrographs of dried ceria-carbon paste coated on conventional printed carbon electrodes.
Figure 16:
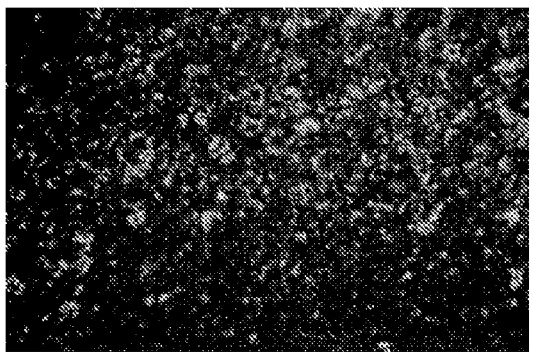
Figure 16:
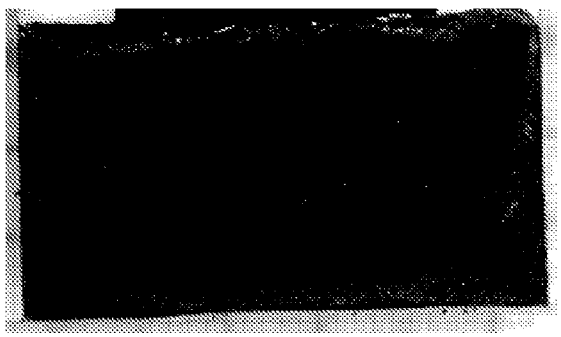
Figure 16:
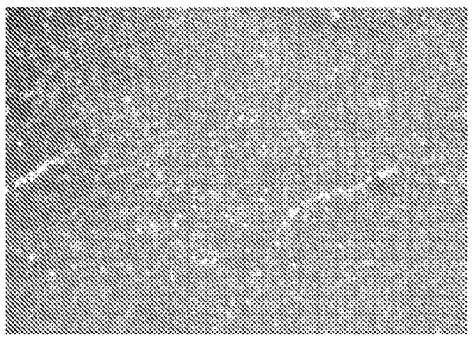

FIG. 16 shows a series of micrographs of dried ceria-carbon paste coated on conventional printed carbon electrodes: single-layer (Panels A and B) and six-layer (Panels C and D). In four batches of single-layer electrodes (total 27) and two batches of double-layer electrodes (total 15), no electrodes had cracking visible to the naked eye or observed under 2× magnification (magnifying glass) or observed under >40× magnification (inspection microscope). In single batches of multi-layer electrodes (5 electrodes per batch), no cracks were seen until 10 layers were applied. At that point, "mud cracking" began, apparently the result of crude drying.

Adhesion.

Single-layer electrodes were examined for material loss with the tape peel test. Neither a weak peel (with a post-it note) nor a moderate peel (with scotch magic tape) removed material visible to the naked eye.

Increase of the Coulombic Capacity with the Number of Applied Layers.

Figure 17:
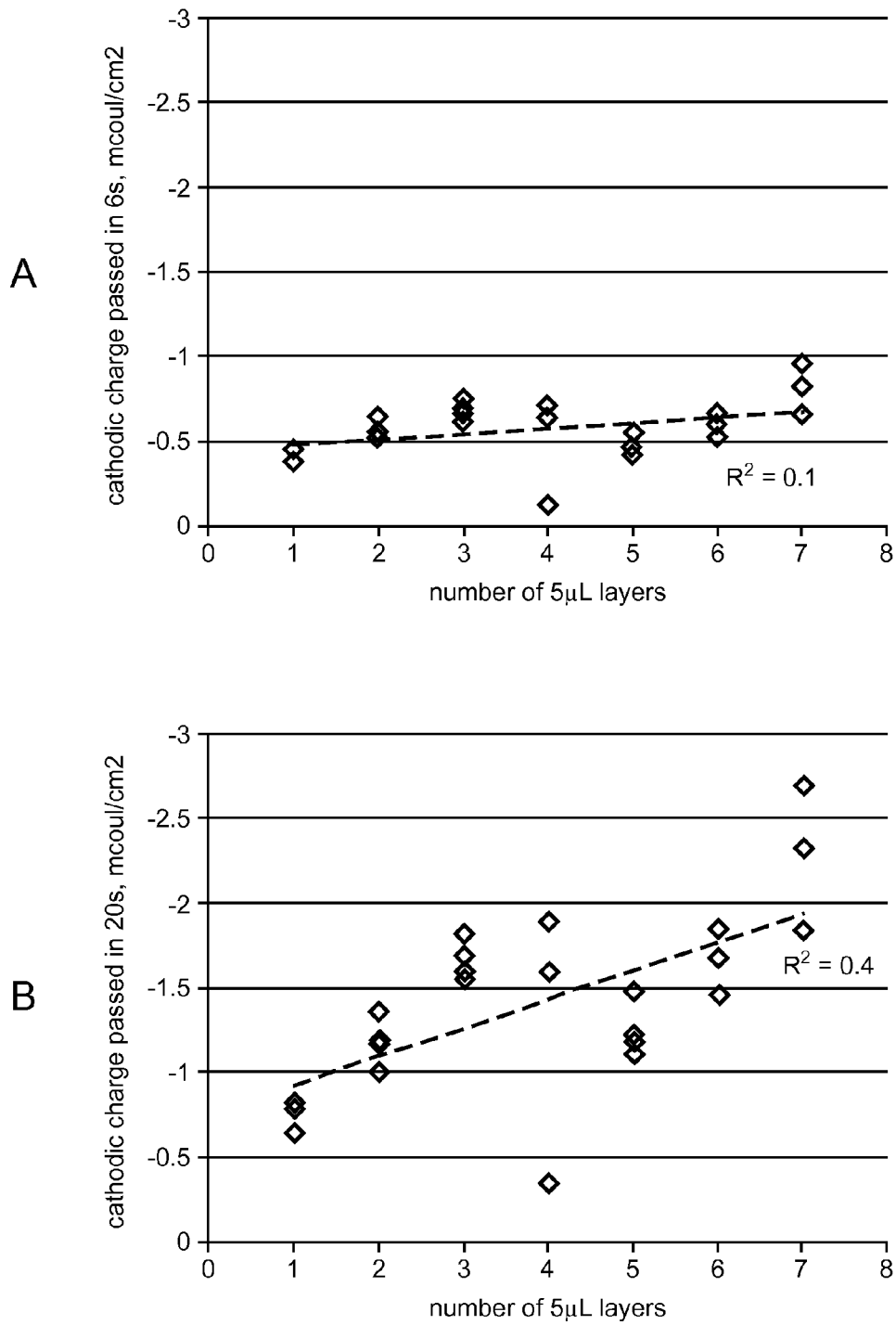
FIGS. 17A-D shows graphs of cathodic charge passed vs. number of layers for ceria electrodes.
Figure 17:
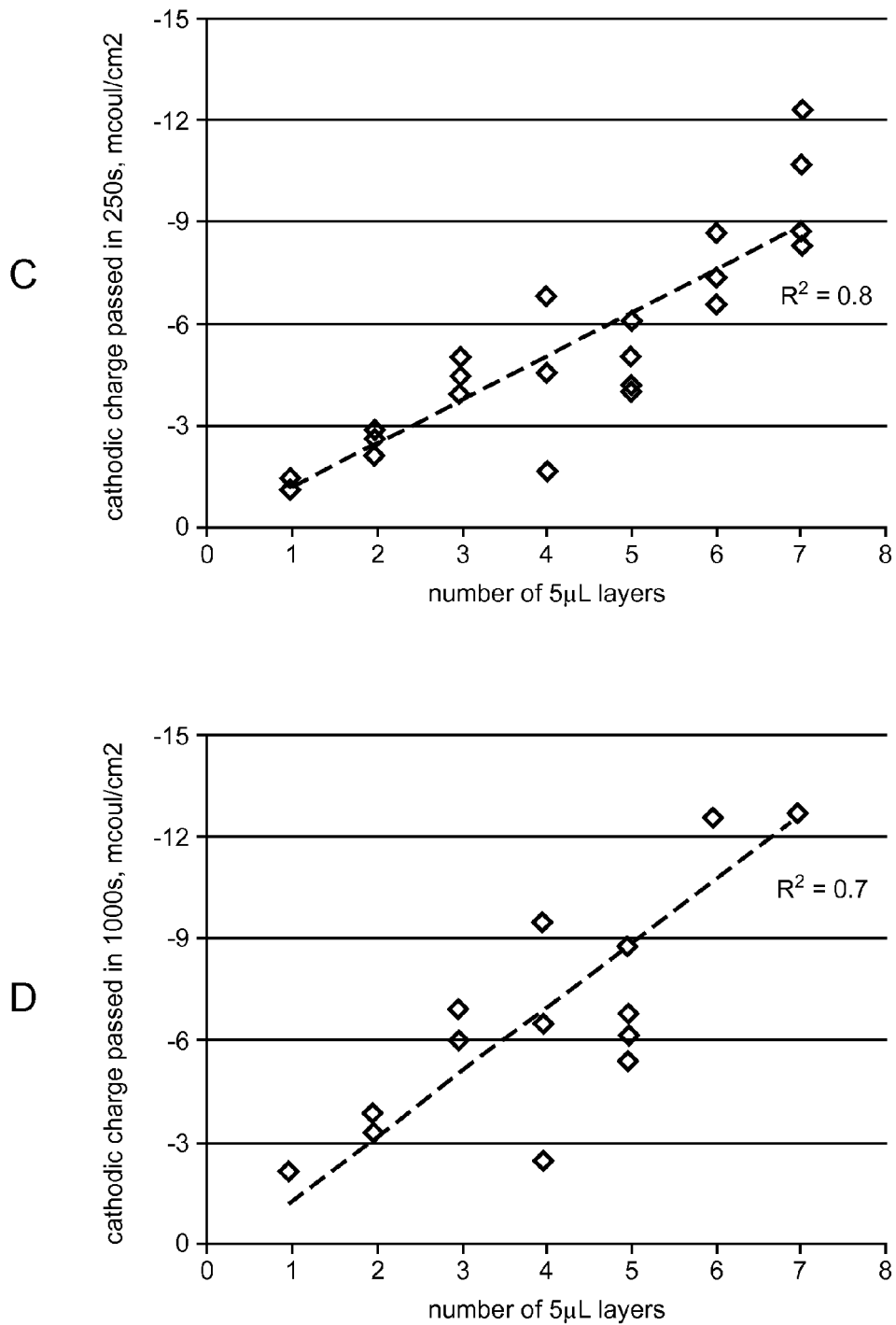

FIG. 17 shows graphs of coulombic capacity of the electrodes as a function of the number of applied layers. While multiple layers had little effect on coulombic capacity at short times (6 s), they had more effect as time increased. From 1 to 7 layers, the capacity increased by a factor of 3 at 20 s, and by a factor of 8-9 at 250 s and 1000 s. The four graphs show charge passed in 6 s (Panel A), 20 s (Panel B), 250 s (Panel C), and 1000 s (Panel D). The vertical axis is cathodic charge passed and it is 0 to −3 mC/cm$^2$ for Panels A and B and 0 to −15 mC/cm$^2$ for Panels C and D. The horizontal axis is number of 5 uL layers, and it is 0 to 7 for all graphs.

The present description should not be considered limited to the particular examples described above, but rather should be understood to cover all aspects as will be readily apparent to those of skill in the art upon review of the instant specification.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. An electrode assembly for an in vitro electrochemical sensor, the electrode assembly comprising:
   a first electrode comprising an analyte responsive enzyme; and
   a second electrode in electrical communication with the first electrode, the second electrode comprising a substrate and a ceria nanoparticle composition applied upon the substrate, the ceria nanoparticle composition having a total mass of ceria nanoparticles per cm$^2$ of substrate area in a range of 0.5 mg/cm$^2$ to 500 mg/cm$^2$.

2. The electrode assembly according to claim 1, wherein the ceria nanoparticles have a particle size from 2 nm to 50 nm.

3. The electrode assembly according to claim 1, wherein the ceria nanoparticle composition comprises a weight percentage of ceria nanoparticles from 10% to 80%.

4. The electrode assembly according to claim 1, wherein the ceria nanoparticle composition further comprises a polymer, the polymer being water soluble or water swellable.

5. The electrode assembly according to claim 1, wherein the ceria nanoparticle composition further comprises a conductive material.

6. The electrode assembly according to claim 1, wherein the ceria nanoparticle composition further comprises a conductive material comprising branched carbon black particles having a diameter of 2 nm to 50 nm.

7. The electrode assembly according to claim 1, wherein the substrate is conductive.

8. The electrode assembly according to claim 1,
   wherein the substrate is non-conductive and is coated with
      a conductive material, the ceria nanoparticle composition being applied upon the conductive material.

9. The electrode assembly according to claim 8, wherein the conductive material comprises gold, platinum, palladium, carbon, indium tin oxide, ruthenium oxide, or doped tin oxide.

10. The electrode assembly according to claim 8, wherein the conductive material comprises a conductive polymer.

11. The electrode assembly according to claim 10, wherein the conductive polymer comprises PEDOT.

12. The electrode assembly according to claim 10, wherein the conductive polymer is polycationic.

13. The electrode assembly according to claim 10, wherein the conductive polymer comprises a polymer of thiophene or of a substituted thiophene; a polymer of pyrrole or of a substituted pyrrole; or a polyacetylene.

14. The electrode assembly according to claim 1, wherein the ceria nanoparticles have the formula $CeO_{2-x}$ and x ranges from 0 to 0.5.

15. The electrode assembly according to claim 14, wherein x ranges from 0.01 to 0.2 for 50% or greater of the ceria nanoparticles.

16. The electrode assembly according to claim 14, wherein x ranges from 0.2 to 0.5 for 50% or greater of the ceria nanoparticles.

17. The electrode assembly according to claim 1, wherein the ceria nanoparticles have the formula $Ce_2O_3$.

18. The electrode assembly according to claim 1, wherein at least a portion of the ceria nanoparticles comprise oxygen anion vacancy defects.

19. The electrode assembly according to claim 18, wherein 1% to 20% of oxygen sites on the portion of the ceria nanoparticles are oxygen anion vacancy defects.

20. The electrode assembly according to claim 1, wherein at least a portion of the ceria nanoparticles are doped with a dopant selected from the group consisting of lanthanum, copper, zinc, cobalt, calcium, aluminum, and any combination thereof, the dopant being present in a range of 1 mole percent to 25 mole percent.

21. The electrode assembly according to claim 1, wherein the total mass of ceria nanoparticles per $cm^2$ of substrate area is in the range of 10 $mg/cm^2$ to 250 $mg/cm^2$.

22. The electrode assembly according to claim 1, wherein the ceria nanoparticle composition further comprises hydrochloric acid.

23. The electrode assembly according to claim 1, wherein the ceria nanoparticle composition further comprises an organic acid in the range of 0.01 w/v % to 1 w/v %.

24. The electrode assembly according to claim 1, wherein the ceria nanoparticle composition further comprises a binder in the range of 1% by weight to 25% by weight.

25. The electrode assembly according to claim 1, wherein the ceria nanoparticle composition further comprises a cationic surfactant in the range of 0.1% by weight to 1% by weight.

26. The electrode assembly according to claim 1, wherein the ceria nanoparticle composition further comprises a cationic surfactant and a binder, a molar ratio of cationic surfactant to binder ranging from 1:1 to 1:1000.

27. The electrode assembly according to claim 1, wherein the first electrode is an anode, and the second electrode is a cathode.

28. The electrode assembly according to claim 1, wherein the first electrode is an anode, and the second electrode is a reference electrode.

29. The electrode assembly according to claim 1, wherein the substrate has a length in a range of 0.1 mm to 5.0 mm, and a width in a range of 0.1 mm to 5.0 mm.

30. The electrode assembly according to claim 1, wherein the ceria nanoparticle composition comprises one or more layers and has a total thickness in a range of 5 μm to 100 μm.

31. The electrode assembly according to claim 1, wherein the ceria nanoparticle composition further comprises a zwitterionic polymer.

* * * * *